US012521490B2

(12) United States Patent
Peliks

(10) Patent No.: US 12,521,490 B2
(45) Date of Patent: Jan. 13, 2026

(54) SYRINGE AND METHOD OF USE

(71) Applicant: Robert Peliks, San Carlos, CA (US)

(72) Inventor: Robert Peliks, San Carlos, CA (US)

( * ) Notice: Subject to any disclaimer, the term of this patent is extended or adjusted under 35 U.S.C. 154(b) by 859 days.

(21) Appl. No.: 17/852,247

(22) Filed: Jun. 28, 2022

(65) Prior Publication Data

US 2023/0108994 A1 Apr. 6, 2023

Related U.S. Application Data

(63) Continuation-in-part of application No. 17/555,458, filed on Dec. 19, 2021, now Pat. No. 11,471,606.

(60) Provisional application No. 63/252,072, filed on Oct. 4, 2021.

(51) Int. Cl.
*A61M 5/315* (2006.01)
*A61M 5/31* (2006.01)

(52) U.S. Cl.
CPC ...... *A61M 5/31528* (2013.01); *A61M 5/3129* (2013.01); *A61M 5/31511* (2013.01); *A61M 2005/3114* (2013.01)

(58) Field of Classification Search
CPC .......... A61M 5/31528; A61M 5/31513; A61M 5/3129; A61M 5/31501; A61M 5/3156; A61M 5/31551; A61M 5/31561
See application file for complete search history.

(56) References Cited

U.S. PATENT DOCUMENTS

| | | | | |
|---|---|---|---|---|
| 1,393,720 | A | 10/1921 | Lomas | |
| 2,283,915 | A | 5/1942 | Cole | |
| 2,736,315 | A | 2/1956 | Feeney | |
| 3,212,685 | A | 10/1965 | James | |
| 3,353,718 | A | 11/1967 | Mclay | |
| 3,938,505 | A | 2/1976 | Jamshidi | |
| 4,275,729 | A | 6/1981 | Silver | |
| 4,583,974 | A | 4/1986 | Kokernak | |
| 4,592,745 | A | 6/1986 | Rex | |
| 5,057,078 | A | 10/1991 | Foote | |
| 5,358,497 | A | 10/1994 | Dorsey | |
| 6,562,007 | B1 * | 5/2003 | Falsey | A61M 5/31551 604/211 |
| 8,939,959 | B2 | 1/2015 | Baney | |
| 9,561,327 | B2 | 2/2017 | Mottola | |
| 2003/0036762 | A1 | 2/2003 | Kerr | |
| 2006/0264837 | A1 | 11/2006 | Bloom | |
| 2011/0313396 | A1 | 12/2011 | Chanoch | |
| 2013/0043282 | A1 | 2/2013 | Niklasson | |
| 2016/0114109 | A1 | 4/2016 | Lavi | |

* cited by examiner

*Primary Examiner* — Michael J Tsai
*Assistant Examiner* — Justin L Zamory

(57) ABSTRACT

A syringe is disclosed. The syringe comprises a plunger and a barrel. The plunger can be rotated relative to the barrel to lock, unlock and/or translate the components relative to each other.

11 Claims, 15 Drawing Sheets

FIG. 1

SYRINGE AND METHOD OF USE

CROSS-REFERENCE TO RELATED APPLICATIONS

This application is a continuation-in-part of U.S. patent application Ser. No. 17/555,458 filed Dec. 19, 2021, which claims priority to U.S. Provisional Application No. 63/252,072, filed Oct. 4, 2021, which are all incorporated by reference herein in their entireties.

BACKGROUND

Technical Field

This disclosure relates to syringes. More particularly, a syringe used to inject or withdraw fluids, such as drugs, medicament, vaccines and the like. More specifically, the present disclosure relates to a method and apparatus for filling, dosing and disposing of a syringe.

Description of the Prior Art

A number of medical procedures require the removal, injection and/or transfer of fluids. Syringes are commonly comprised of three components: a barrel, a plunger & a plunger stopper. The plunger stopper can seal against the inside diameter of the barrel. The plunger stopper can be longitudinally and/or rotationally fixed with respect to the plunger, such that advancing or retracting the plunger within the barrel can withdraw or inject fluids through the nozzle of the barrel. The plunger and/or plunger stopper can be slidably mounted and retractable/advanceable within the barrel. The syringe can be comprised of a barrel & a plunger; the plunger can form a seal with the barrel without the need for a separate plunger stopper. At least one component of the syringe can be marked with graduation lines to indicate the volume of fluid retained in the syringe. Graduation lines can be evenly spaced and labeled as mL, uL, units, cc, cubic centimeters, oz, grams and/or insulin units; other scales and/or units can be used. A lubricant, such as silicone, can be applied to the syringe to reduce friction between the barrel, plunger stopper and/or plunger while maintaining an adequate fluid seal.

Syringes can be available in various volumes; including, but not limited to 0.25 mL, 0.3 mL, 0.5 mL, 1 mL, 1.2 mL, 2.5 mL, 5 mL, 6 mL, 10 mL, 20 mL, 30 mL, 50 mL and 60 mL. Syringes can be actuated by pushing or pulling the plunger and/or the plunger stopper with respect to the barrel. Syringes can include a continuous thread feature. Syringes can be actuated by rotating the plunger with respect to the barrel; rotation can yield more controlled and/or precise dosage than translation of the plunger alone.

Syringes can include features to lock the plunger at different locations with respect to the barrel. For example, an operator can advance or retract the plunger to a set point, lock the syringe at that set point & wait for the pressure to equalize between the inside of the syringe & a cavity in communication with the syringe. The operator can unlock the plunger position to adjust the syringe volume.

Syringes can be used once or multiple times. Syringes can be clean, sterilized, re-sterilizable and/or unsterile.

SUMMARY

A syringe used to transfer and/or store fluids is disclosed herein. The syringe can have a barrel and a plunger. The syringe can have a barrel, a plunger, a plunger stopper and/or a barrel nut. The plunger stopper can be longitudinally fixed with respect to the plunger. The plunger can have a plunger thread face that can include a discontinuous external thread. The barrel and/or the barrel nut can have a barrel thread face that can include a discontinuous internal thread. The barrel and the barrel nut can be longitudinally and/or rotationally fixed with respect to each other. The barrel thread face can be an unthreaded feature that can engage with the plunger thread face; for example, the barrel thread face and/or the plunger thread face can have a tab, a discontinuous thread, a continuous thread, a dimple, a boss, a flexible material, a cylinder and/or a hole. In some rotational alignments, the plunger thread face and the barrel thread face can be in an engaged configuration with respect to each other; in other rotational alignments, the plunger thread face and the barrel thread face can be in a disengaged configuration with respect to each other. In the engaged configuration the plunger thread face and the barrel thread face can be in contact with each other. In the disengaged configuration, the plunger thread face and the barrel thread face can not be in contact with each other and/or have partial contact with each other. When in the disengaged configuration, the relative longitudinal position of the plunger with respect to the barrel can be adjusted by longitudinally translating the two components with respect to each other. For example, when in the disengaged configuration, the plunger can be depressed and translate with respect to the barrel. The plunger can be depressed and/or pulled at a push button. When in the engaged configuration, the plunger & the barrel can be longitudinally fixed with respect to each other. The force to translate the plunger with respect to the barrel can be higher in the engaged configuration than in the disengaged configuration. When in the engaged configuration, the plunger can be unable to translate without rotation relative to the barrel. When rotating from the disengaged configuration to the engaged configuration (or when rotating from the engaged configuration to the disengaged configuration), the plunger & the barrel can translate with respect to each other. When rotating the plunger with respect to the barrel in the engaged configuration, the plunger & the barrel can translate with respect to each other. Rotating the barrel and the plunger clockwise or counter-clockwise with respect to each other can advance and/or retract the plunger with respect to the barrel. The amount of relative translation between the plunger and the barrel caused when rotating the plunger with respect to the barrel can be controlled by the pitch, arc length, arc angle of features on the barrel thread face and/or arc angle of features on the plunger thread face. The barrel thread face can be located in a barrel engagement region. The plunger thread face can be located in a plunger engagement region.

The barrel thread face and/or the plunger thread face can be shaped to minimize interaction with other components of the syringe. For example, the barrel thread face and/or plunger thread face can have a trapezoidal, quadrilateral, triangular, polygonal and/or rounded cross-section. The barrel thread face, the plunger thread face and/or other features of the syringe can be shaped to minimize interaction with other features of the syringe when pushing or pulling the plunger with respect to the barrel in the disengaged configuration or in a partially engaged configuration (i.e., at the transition of the engaged & the disengaged configurations). The barrel thread face, plunger thread face and/or other features of the syringe can be shaped to maximize or control interaction with other features of the syringe when pushing or pulling the plunger with respect to the barrel (e.g., the user can hear and/or feel a tactile "click" when pushing or pulling the plunger with respect to the barrel).

The syringe may have a barrel having a barrel body having a barrel thread face across a barrel thread face arc angle at a first cross-section. The barrel thread face may have an internal barrel thread integral with the barrel body. An inner cross-section of the barrel at the first cross-section may be oval. The inner cross-section of the barrel at a second cross-section may be circular. The syringe may have a plunger having a plunger body At least a length of the plunger body may be in the bare. The plunger can have a plunger thread face across a plunger thread face arc angle at the first cross-section. The plunger thread face can have a first and second external plunger threads integral with the plunger body. In a first configuration the plunger can be rotated 0 degrees with respect to the barrel and the barrel can be at a first longitudinal position with respect to the plunger. In a second configuration the plunger can be rotated more than 360 degrees with respect to the barrel and the barrel can be at the first second longitudinal position with respect to the plunger. In the first configuration the internal barrel thread can be engaged with the first and second external plunger threads. In the second configuration the internal barrel thread can be engaged with the first and second external plunger threads.

The barrel thread face arc angle added to the plunger thread face arc angle at the first cross-section can be less than 360 degrees. The plunger threads and the barrel threads can be perpendicular with a longitudinal axis of the syringe. The plunger and the barrel threads can be not engaged when the syringe is in a third configuration.

The barrel at the second cross-section can not have threads.

The inner cross-section of the barrel at a third cross-section can be circular, and a longitudinal position of the third cross-section can be on an opposite side of a longitudinal position of the first cross-section from a longitudinal position of the second cross-section.

An inner surface of the barrel can have a lofted transition from the third cross-section to the first cross-section and can have a lofted transition from the first cross-section to the second cross-section.

The plunger can be fully removable from the barrel when the syringe is assembled.

The plunger can have an oblong plunger head and the barrel can have an oblong barrel flange.

A minimum outer radius at a length of the barrel body collinear with the barrel thread face can be less than minimum outer radius at a length of the barrel body longitudinally adjacent to the barrel thread face.

The first cross-section can be symmetric about a major axis and is symmetric about a minor axis.

A syringe for dispensing a fluid can have a barrel having a barrel body having a barrel thread face across a barrel thread face arc angle at a first cross-section. The barrel thread face can have an internal barrel thread integral with the barrel body. An inner cross-section of the barrel at the first cross-section can have a first minimum inner diameter and a first maximum inner diameter. The inner cross-section of the barrel at a second cross-section can have a second minimum inner diameter and a second maximum inner diameter. The first minimum inner diameter can be smaller than the second minimum inner diameter. The first maximum inner diameter can be larger than the second maximum inner diameter. The inner cross-section of the barrel at a third cross-section can have a third minimum inner diameter and a third maximum inner diameter. A longitudinal position of the third cross-section can be on an opposite side of a longitudinal position of the first cross-section from a longitudinal position of the second cross-section. The first minimum inner diameter can be smaller than the third minimum inner diameter. The second minimum inner diameter can be equal to the third minimum inner diameter. The second maximum inner diameter can be equal to the third maximum inner diameter. The syringe can have a plunger having a plunger body. At least a length of the plunger body can be in the barrel. The plunger can have a plunger thread face across a plunger thread face arc angle at the first cross-section. The plunger thread face can have first and second external plunger threads integral with the plunger body. The barrel threads can be perpendicular with a longitudinal axis of the syringe.

In a first configuration the plunger can be rotated 0 degrees with respect to the barrel and the barrel can be at a first longitudinal position with respect to the plunger. In a second configuration the plunger can be rotated 360 degrees with respect to the barrel and the barrel can be at the first longitudinal position with respect to the plunger. In the first configuration the internal barrel thread can be engaged with the first and second external plunger threads. In the second configuration the internal barrel thread can be engaged with first and second external plunger threads.

A detent extending from the barrel body can be at the first minimum inner diameter.

An inner surface of the barrel can have a lofted transition from the third cross-section to the first cross-section and can have a lofted transition from the first cross-section to the second cross-section.

A method for dispensing a fluid using a syringe can comprise a plunger having a plunger body having a plunger thread integral with the plunger body and a barrel having a barrel body having a barrel thread integral with the barrel body at a first cross-section. The method may comprise longitudinally depressing the plunger with respect to the barrel when the plunger starts at a first angular position. The depressing can result in longitudinal translation of the plunger with respect to the barrel. The depressing can comprise contacting the barrel thread with the plunger. The method may comprise rotating the plunger with respect to the barrel when the plunger starts at the first angular position with respect to the barrel. The rotating can comprise engaging the plunger thread with the barrel thread. The method may comprise pressing the plunger with respect to the barrel when the plunger starts at a second angular position with respect to the barrel. The pressing of the plunger can comprise no longitudinal translation of the plunger with respect to the barrel. An inner cross-section of the barrel at the first cross-section can have a first minimum inner diameter. The inner cross-section of the barrel at a second cross-section can have a second minimum inner diameter. The first minimum inner diameter can be smaller than the second minimum inner diameter. The inner cross-section of the barrel at a third cross-section can have a third minimum inner diameter. A longitudinal position of the third cross-section can be on an opposite side of a longitudinal position of the first cross-section from a longitudinal position of the second cross-section. The first minimum inner diameter can be smaller than the third minimum inner diameter.

Rotating can not longitudinally move the plunger with respect to the barrel.

The pressing and/or the rotating can comprise the plunger being threadably engaged with the barrel. The depressing can comprise the plunger being threadably disengaged from the barrel.

The rotating can comprise rotating more than 360 degrees.

A first radial distance from the plunger thread to a longitudinal axis of the plunger when rotating the plunger can be equal to a second radial distance from the plunger thread to the longitudinal axis of the plunger when depressing the plunger. A third radial distance from the barrel thread to the longitudinal axis of the plunger when rotating the plunger can be equal to a fourth radial distance from the barrel thread to the longitudinal axis of the plunger when depressing the plunger.

The pressing, rotating and/or depressing can start with the plunger at a first longitudinal position with respect to the barrel.

The barrel can have a first outer radius. The rotating can comprise deforming the barrel. The deforming of the barrel can comprise increasing the first outer radius.

The minimum external radial distance in the threaded region of the barrel may be less than the minimum barrel external radial distance proximal or distal to the threaded region of the barrel. The barrel outside cross-section may be oval, non-circular and/or oblong at the threaded region of the barrel. The barrel flange and the plunger button may have similar profiles. Having similar profiles of the barrel flange and the plunger may provide a visual indication of the syringe configuration. Having similar profiles of the barrel flange and the plunger may be useful in manufacturing; for example, to orient the components during assembly. Having similar profiles of the barrel flange and the plunger may provide easier gripping of the components (e.g., to rotate the components relative to each other). The barrel thread may be formed in a secondary operation (e.g., the barrel may be first injection molded and then undergo a secondary operation where a portion of the barrel may be compressed around an insert to form the barrel threads). The barrel insert may be a threaded cylinder. The syringe may be a unibody syringe.

BRIEF DESCRIPTION OF THE DRAWINGS

FIG. 2A is an illustrative view with a left half of the barrel removed, FIG. 2B is a detailed view of the proximal end of the barrel engagement region and the plunger engagement region illustrated in FIG. 2A, and FIG. 2C is the same detailed view as FIG. 2B with the plunger removed.

FIG. 6*a* and FIG. 6*b* use the plunger illustrated in FIG. 3B. FIG. 6A illustrates the syringe in an engaged configuration. FIG. 6B illustrates the syringe in a disengaged configuration.

FIG. 7A and FIG. 7B show the plunger illustrated in FIG. 3E. FIG. 7A illustrates the syringe in the engaged configuration. FIG. 7B illustrates the syringe in the disengaged configuration.

FIG. 14*a* is an isometric view of the plunger and FIG. 14*b* is a side view of a short section of the plunger illustrated in FIG. 14*a*. FIG. 14*c* and FIG. 14*d* illustrate a cross-sectional view of the barrel nut with the longitudinal axis perpendicular to the page.

FIG. 16*a* illustrates the plunger in an isometric view. FIG. 16*b* illustrates a cross-section of the plunger in the plunger engagement region, with the longitudinal axis perpendicular to the page. FIG. 16*c* and FIG. 16*d* illustrate two side views of a short section of the plunger, rotated 90 degrees from each other about the longitudinal axis.

FIG. 18*a* illustrates a portion of the barrel engagement region in an isometric view and FIG. 18*b* illustrates a portion of the plunger engagement region in an isometric view. FIG. 18*c* illustrates a cross-section of the barrel and the plunger at the barrel and plunger engagement regions in the disengaged configuration, with the longitudinal axis perpendicular to the page. FIG. 18*d* illustrates a cross-section of the barrel and the plunger at the barrel and plunger engagement regions in the engaged configuration, with the longitudinal axis perpendicular to the page.

FIG. 20 is the same view as in FIG. 8, however FIG. 20 illustrates a different barrel thread design than that shown in FIG. 8

FIG. 21*a* through FIG. 21*i* illustrate the plunger rotating 360 degrees clockwise with respect to the barrel in 45 degree increments per figure & a resultant advancement of the plunger in the distal direction caused by the rotation.

FIG. 26*a* through FIG. 26*e* illustrate the plunger rotating 180 degrees clockwise with respect to the barrel in 45 degree increments per figure.

FIG. 29 is the same view as in FIG. 8, however FIG. 29 illustrates a different barrel thread design than that shown in FIG. 8.

DETAILED DESCRIPTION

Figure 1:
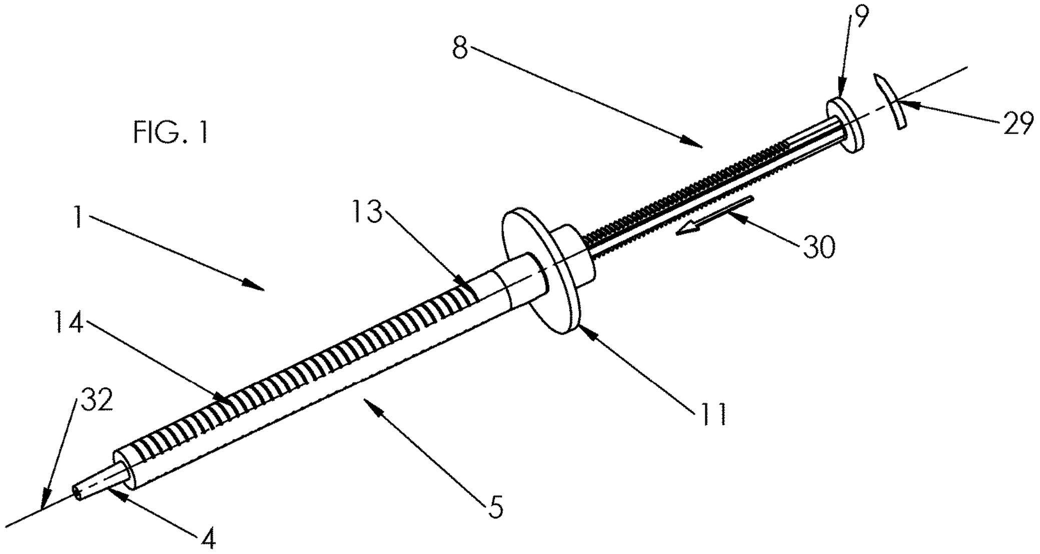
FIG. 1 is an illustrative isometric view of the syringe.

FIG. 1 illustrates a syringe 1 that can be cleaned, sterilized and/or unsterilized. The syringe 1 can be provided in clean and or sterile packaging. For example, the syringe 1 can be packaged in a plastic, tyvek and/or a sterile pouch. Methods to sterilize the syringe 1 can include steam, Ethylene Oxide, Hydrogen Peroxide Gas Plasma, peracetic acid, ionizing radiation, dry heat, performic acid, microwave, glass bead, vaporized hydrogen peroxide, ozone, formaldehyde steam, radiation, gaseous chlorine dioxide, vaporized peracetic acid, infrared radiation and/or e-beam. A longitudinal axis 32 is shown for illustrative purposes. The syringe 1 can have a barrel 5 and a plunger 8. The barrel 5 can have a nozzle 4, graduation lines 14, a mark and/or the graduation line 14 indicating a nominal capacity 13, and a barrel flange 11. The plunger 8 can have a push button 9. The plunger 8 can be moved relative to the barrel 5 in a distal direction 30, in a proximal direction opposite the distal direction 30, in a clockwise direction 29 and/or in a counterclockwise direction opposite the clockwise direction 29. The barrel 5 and/or the plunger 8 can have features (such as a bump off) to help keep the plunger 8 inside of the barrel 5. The nozzle 4 can be a luer slip tip, a slip tip, a luer lock tip, an eccentric tip, a barb, a catheter tip, an EnFit tip, a UniVia tip, an enteral tip and/or a toomey tip. The nozzle 4 can be other geometries. A hypodermic needle can be secured to the nozzle 4. A tube can be secured to the nozzle 4. The nozzle 4 can be configured to be secured to a polymer tube, a metal tube, a hypodermic needle and/or other components. The nozzle 4 can be configured to be secured to a tube with multiple materials (e.g., a polymer tube with a metal braid).

Figure 2A:
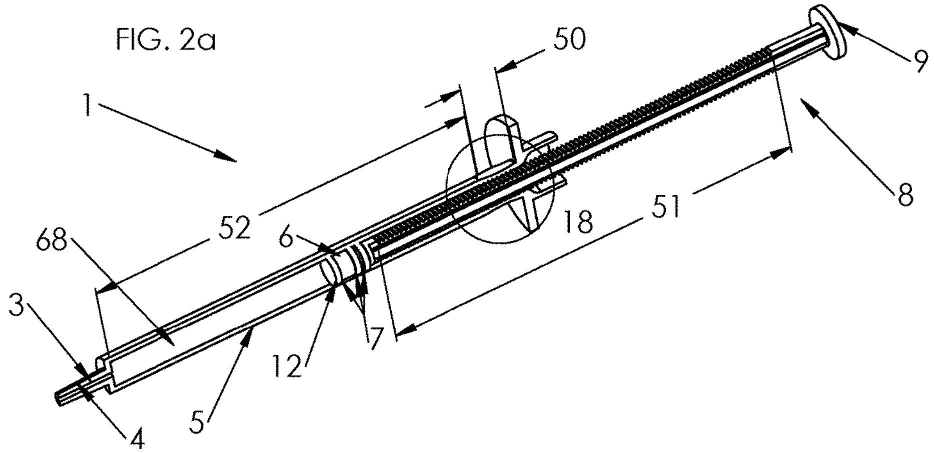
FIG. 2A through FIG. 2C are illustrative isometric views of the syringe with different sections removed.

FIG. 2A illustrates that a nozzle lumen 3 can be in fluid communication with the inside diameter of the barrel 5. The nozzle lumen 3 can allow fluid to transfer into and/or out of the syringe 1. A plunger stopper 6 can be secured to the plunger 8. The plunger stopper 6 can be longitudinally and/or rotationally secured to the plunger 8. The plunger stopper 6 and/or the plunger 8 can have a seal 7. The seal 7 can seal along the inside circumference of the barrel 5. The seal 7 can seal along a barrel inner surface 68. The plunger stopper 6 can have multiple seals 7. The seals 7 can be integral to the plunger stopper 6 and/or the plunger 8. The seals 7 can be raised ridges, circles and/or rings on the plunger stopper 6. The plunger stopper 6 can be rubber, thermoplastic elastomer (TPE), polyisoprene rubber, latex-free elastomer, silicone, liquid silicone rubber (LSR), polypropylene, ABS, PC, glass, LDPE and/or HDPE. The plunger stopper 6 can be a separate component than the plunger 8. The plunger stopper 6 can be an o-ring, an x-ring, a double x ring and/or a backup ring. For example, the plunger 8 can have a groove to accept and/or secure the plunger stopper 6 o-ring. The plunger stopper 6 and the plunger 8 can be the same component. The plunger stopper 6 and/or the plunger 8 can have a fiducial line 12. The fiducial line 12 in conjunction with the graduation lines 14 can indicate the volume of fluid contained within the syringe 1. The plunger 8 can have a plunger body. The plunger body can have a plunger engagement region 51. The barrel 5 can have a barrel body. The barrel body can have a barrel sealing region 52 and/or a barrel engagement region 50. The seal 7 can provide a fluid-tight seal in the barrel sealing region 52 and/or the barrel engagement region 50. A first detail view 18 is shown in greater detail in FIG. 2B.

Figure 2B:
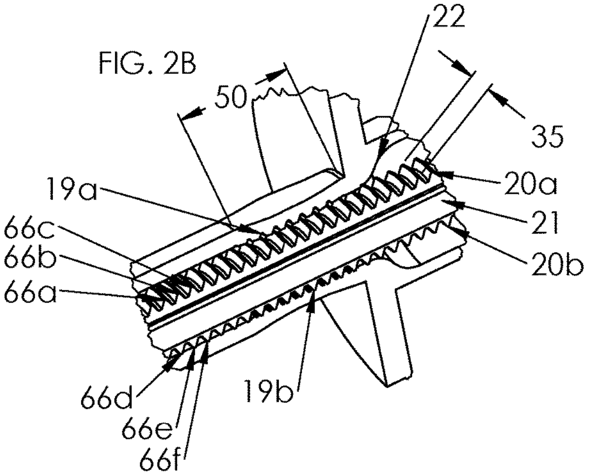

FIG. 2B illustrates that the barrel 5 can have the barrel engagement region 50. The barrel 5 can have a barrel thread face 19*a* and/or 19*b* located in the barrel engagement region 50. The plunger 8 can have a plunger thread face 20*a* and/or 20*b* located in the plunger engagement region 51. The plunger thread face 20 can engage with the barrel thread face 19. The syringe 1 and/or the plunger 8 can have one or multiple plunger thread face 20. The syringe 1 and/or the barrel 5 can have one or multiple barrel thread face 19. The syringe 1 and/or the plunger 8 can have a plunger unthreaded face 21. The syringe 1 and/or the plunger 8 can have one or multiple plunger unthreaded faces 21. The barrel 5 can have a barrel ramp 22. The barrel ramp 22 can be straight and/or curved. The barrel ramp 22 can allow a smooth transition when the plunger 8 is moved with respect to the barrel 5. For example, if the plunger 8 is bent and/or angled with respect to the barrel 5 when translated with respect to each other, the barrel ramp 22 can prevent the plunger thread face 20 from catching on the proximal end of the barrel 5. The barrel ramp 22 can be designed to catch the plunger thread face 20. For example, the barrel ramp 22 can contact the plunger thread face 20 and can provide tactile and/or auditory feedback when the plunger 8 is translated with respect to the barrel 5. The plunger 8 can have a plunger thread 66 and/or multiple plunger threads 66. The plunger threads 66 can be in the plunger engagement region 51.

Figure 2C:
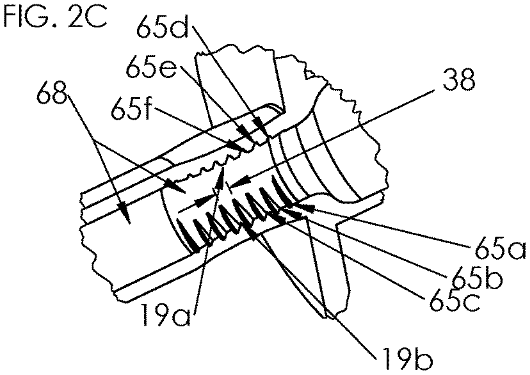

FIG. 2C illustrates that the barrel thread faces 19*a* and/or 19*b* can be formed in the barrel 5. The barrel thread faces 19 can be formed in the barrel inner surface 68. The barrel thread faces 19 can be formed by compressing the barrel 5 around a tool temporarily located inside of the barrel 5. The barrel thread faces 19 can be machined, laser cut, melted, vaporized, stamped, molded, formed, thermoformed, tapped and/or cut into the barrel 5. The barrel thread faces 19 can be injection molded, overmolded and/or two shot molded. The barrel thread faces 19 can have one or multiple barrel thread 65. The barrel thread faces 19 can have a barrel thread pitch 38. The plunger threads 66 and/or the barrel threads 65 can be continuous and/or discontinuous. The barrel thread pitch 38 can be the distance between two barrel threads 65 on the same barrel thread face 19 measured along the longitudinal axis 32. The barrel thread faces 19 and/or the plunger thread faces 20 can be continuous and/or discontinuous. The barrel threads 65 on the barrel thread faces 19 can have one or multiple thread starts. The plunger threads 66 on the plunger thread faces 20 can have one or multiple thread starts. The barrel threads 65 on the barrel thread faces 19 can be holes, slits and/or slots that pass through the entire wall of the barrel 5. The barrel thread faces 19 can pass through a portion of the wall of the barrel 5. The barrel thread face 19 can be formed by heating the barrel 5 and/or the barrel engagement region 50, and then compressing the barrel engagement region 50 over a tool.

The barrel sealing region 52, the barrel engagement region 50 and/or the plunger engagement region 51 can have a cross-section that is circular, oval, oblong, rectangular, triangular and/or polygonal. The inside and/or outside diameter of the barrel in the barrel sealing region 52 and/or the barrel engagement region 50 can be larger than 0.05 in (1.27 mm), yet more narrowly larger than about 0.10 in (2.54 mm), yet more narrowly larger than about 0.15 in (3.81 mm), yet more narrowly larger than about 0.20 in (5.08 mm), yet more narrowly larger than about 0.25 in (6.35 mm), yet more narrowly larger than about 0.30 in (7.62 mm), yet more narrowly larger than about 035 in (8.89 mm), yet more narrowly larger than about 0.4 in (10.16 mm), yet more narrowly larger than about 0.45 in (11.43 mm), yet more narrowly larger than about 0.5 in (12.7 mm), yet more narrowly larger than about 0.55 in (13.97 mm), yet more narrowly larger than about 0.6 in (15.24 mm), yet more narrowly larger than about 0.65 in (16.51 mm), yet more narrowly larger than about 0.7 in (17.78 mm), yet more narrowly larger than about 0.75 in (19.05 mm), yet more narrowly larger than about 0.8 in (20.32 mm), yet more narrowly larger than about 0.9 in (22.86 mm), yet more narrowly larger than about 1.0 in (25.4 mm), yet more narrowly larger than about 1.1 in (27.94 mm) or yet more narrowly larger than about 1.2 in (30.48 mm). The inside and/or outside diameter of the barrel 5 in the barrel sealing region 52 and/or the barrel engagement region 50 can be smaller than 1.5 in (30.48 mm), yet more narrowly smaller than about 1.1 in (27.94 mm), yet more narrowly smaller than about 1.0 in (25.4 mm), yet more narrowly smaller than about 0.9 in (22.86 mm), yet more narrowly smaller than about 0.8 in (20.32 mm), yet more narrowly smaller than about 0.75 in (19.05 mm), yet more narrowly smaller than about 0.7 in (17.78 mm), yet more narrowly smaller than about 0.65 in (16.51 mm), yet more narrowly smaller than about 0.6 in (15.24 mm), yet more narrowly smaller than about 0.55 in (13.97 mm), yet more narrowly smaller than about 0.5 in (12.7 mm), yet more narrowly smaller than about 0.45 in (11.43 mm), yet more narrowly smaller than about 0.4 in (10.16 mm), yet more narrowly smaller than about 0.35 in (8.89 mm), yet more narrowly smaller than about 0.3 in (7.62 mm), yet more narrowly smaller than about 0.25 in (6.35 mm), yet more narrowly smaller than about 0.2 in (5.08 mm), yet more narrowly smaller than about 0.15 in (3.81 mm), yet more narrowly smaller than about 0.1 in (2.54 mm) or yet more narrowly smaller than about 0.05 in (1.27 mm). The inside and/or outside diameter of the barrel 5 can vary in different locations.

Figure 3A:
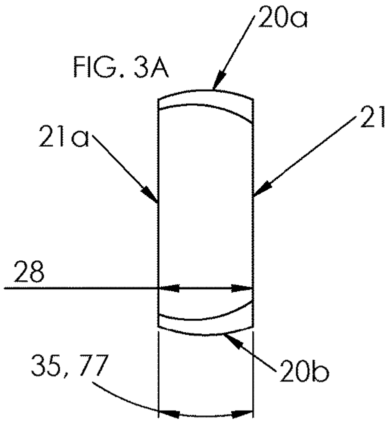
FIG. 3A through FIG. 3H are cross-sectional views of different plunger designs, with a longitudinal axis perpendicular to the page.

FIG. 3A illustrates that the plunger 8 can have the plunger thread faces 20*a* and/or 20*b*. The plunger 8 can have the plunger unthreaded faces 21*a* and/or 21*b*. The plunger thread faces 20 and the plunger unthreaded faces 21 can be located in the plunger engagement region 51. The plunger can have one or multiple plunger thread face 20 and/or plunger unthreaded face 21. The plunger threads 65 on the plunger thread face 20*a* can line up with the plunger threads 65 on the plunger thread face 20*b*; for example, a nut can be able to simultaneously engage with the plunger threads 65 on the plunger thread face 20*a* and 20*b*. The barrel threads 66 on the barrel thread face 19*a* can line up with the plunger threads 66 on the barrel thread face 19*b*; for example, a screw can be able to simultaneously engage with the barrel threads 66 on the barrel thread face 19*a* and 19*b*. The plunger threads 65 on the plunger thread faces 20*a* and/or 20*b* can simultaneously engage with the barrel threads 66 on the barrel thread faces 19*a* and/or 19*b*. The plunger unthreaded faces 21*a* and 21*b* can be symmetrical or asymmetrical. The plunger threads 65 can have one or multiple thread starts. A plunger flat width 28 can be small enough to ensure that the plunger unthreaded faces 21 do not contact the barrel thread faces 19. The maximum radial distance of the plunger unthreaded face 21 can be less than the maximum radial distance of the plunger thread face 20. The maximum radial distance of the plunger unthreaded face 21 can be less than the minimum radial distance of the barrel thread face 19. The plunger flat width 28 can be less than the minor, pitch and/or major diameter of the plunger threads 65. The plunger flat width 28 can be large enough to provide adequate compression, tensile, axial, bending and/or torsional strength to the plunger 8. A plunger thread arc length 35 and/or a plunger thread face arc length 77 can be adequately large enough to engage with the barrel thread faces 19. The plunger thread arc length 35 and/or the plunger thread face arc length 77 can be the same or different for the plunger thread faces 20*a* and 20*b*. The plunger thread arc length 35 can be the three dimensional length of the plunger thread 66 at the major, minor and/or pitch diameter. For example, the plunger thread arc length 35 can be longer for a coarser pitched plunger thread 66 than a shallower pitcher plunger thread 66, even if they have the same plunger thread face arc angle 37. The plunger thread face arc length 77 can be the two dimensional curved length of the plunger thread face 19 at a given cross-section. The plunger thread arc length 35 can be less than, equal to or greater than the plunger thread face arc length 77. For example, the plunger thread face 20 can have staggered and/or overlapping plunger threads 65. The plunger thread face arc angle 37 can be the maximum angle from one end of the plunger thread 65 to the other end of the same plunger thread 66, with the vertex at the longitudinal axis 32. The plunger thread arc face angle 77 can be the maximum angle from one end of the plunger thread face 20 to the other end of the plunger thread face 20, with the vertex at the longitudinal axis 32.

Figure 3B:
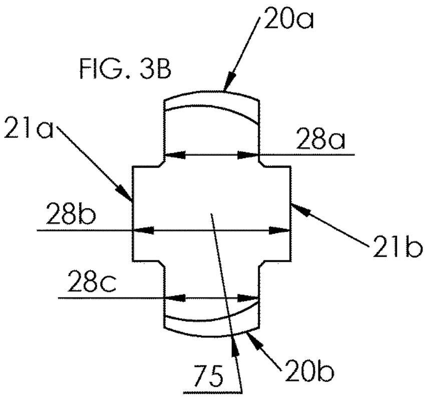
Figure 3C:
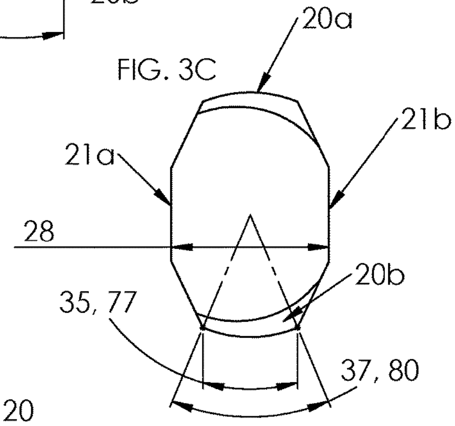
Figure 3D:
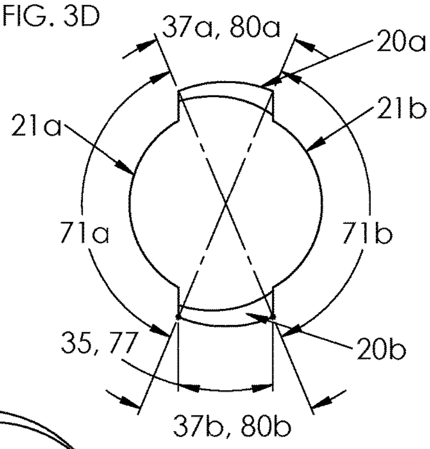
Figure 3E:
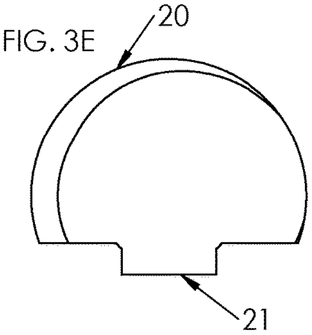
Figure 3F:
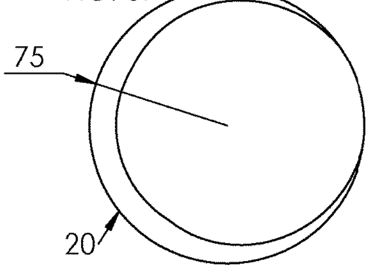
Figure 3G:
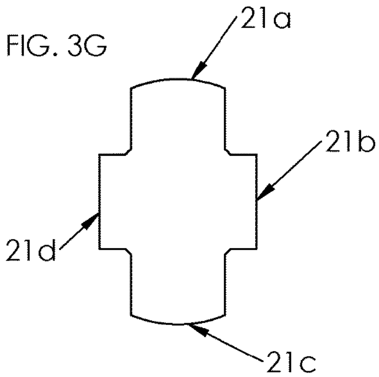
Figure 3H:
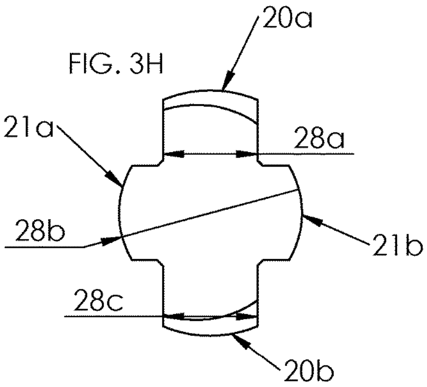

FIG. 3B illustrates that the plunger flat width 28 can vary across the cross-section of the plunger 8. The plunger 8 can have multiple plunger flat widths 28*a*, 28*b* and/or 28*c*. For example, the profile illustrated in FIG. 3B can be beneficial if the plunger 8 is injection molded, to minimize material and/or to maximize component strength. The plunger 8 can have one or multiple flat widths 28. FIG. 3C illustrates that the plunger thread faces 20 can be connected to the plunger unthreaded faces 21 with an angled and/or curved face. The angled and/or curved face connecting the plunger thread faces 20 to the plunger unthreaded faces 21 can provide a smooth transition when the plunger thread faces 20 engage and/or disengage with the barrel thread faces 19. The plunger unthreaded face 21 can be flat, curved and/or polygonal. For example, the plunger unthreaded face 21 can be all faces that are not the plunger thread face 20. FIG. 3D illustrates that the plunger unthreaded faces 21*a* and/or 21*b* can have a round cross-section. For example, the plunger unthreaded faces 21*a* and/or 21*b* can have a diameter equal to or smaller than the minor diameter, pitch diameter and/or major diameter of the plunger threads 66. The plunger unthreaded faces 21*a* and/or 21*b* can be enclosed by an imaginary circle formed by a minor, pitch and/or major diameter of the plunger thread(s) 66. A plunger thread face arc angle 37 can define the arc angle of the plunger thread faces 20, with the longitudinal axis 32 at the vertex of the angle. The plunger 8 can have one or multiple of the plunger thread faces 20 and/or the plunger unthreaded faces 21. FIG. 3E illustrates that the plunger 8 can have one plunger thread face 20 and one plunger unthreaded face 21. FIG. 3F illustrates that the plunger 8 can have one plunger thread face 20 and no plunger unthreaded face 21; for example, the entire outside circumference and/or diameter of the plunger 8 can be threaded. FIG. 3G illustrates that the plunger 8 can have one plunger unthreaded face 21 or multiple plunger unthreaded faces 21*a*, 21*b*, 21*c* and/or 21*d*. FIG. 3H illustrates that the plunger unthreaded face 21 and/or plunger flat width 28*b* can be curved. The plunger flat width 28*b* can be equal to or less than the minor, pitch and/or major diameter of the plunger thread 66 on the plunger thread face 20. The plunger 8 can have no plunger thread face 20. The plunger unthreaded face 21 and/or the plunger thread face 20 can have a round, linear and/or polygonal cross-sectional profile. The outside diameter of plunger 8 can be circular, triangular, quadrilateral, polygonal and/or oval. The cross-section of the plunger 8 can vary along its length. For example, the plunger 8 can include multiple cross-sections, including but not limited to those shown in FIG. 3A-FIG. 3H. A plunger unthreaded face arc angle 71 can define the arc angle of the plunger unthread faces 21, with the vertex of the angle at the longitudinal axis 32. The plunger 8 can have a plunger thread radial distance 75. The plunger thread radial distance 75 can be constant. The plunger thread radial distance 75 can vary over the length of the plunger 8 and/or over time. The plunger thread radial distance 75 can be the distance from the longitudinal axis 32 to the major, minor, maximum, minimum and/or pitch diameter of the plunger thread 66 and/or plunger thread face 20. The plunger thread radial distance 75 can be approximately half of the distance between two opposing plunger thread faces 20*a* and 20*b*. The plunger thread radial distance 75 can be approximately half of the distance between two opposing plunger threads 66*a* and 66*b*. The plunger thread radial distance 75 can be measured perpendicular to the longitudinal axis 32. The plunger 8 can have a plunger thread arc angle 80. The plunger thread arc angle 80 can be greater, less than or equal to the plunger thread face arc angle 37. For example, the plunger 8 can include different length or angle plunger threads 66*a* and 66*b* on the plunger thread face 20. The plunger thread arc angle 80 can define the arc angle of the plunger thread 66, with the vertex of the angle at the longitudinal axis 32

Figure 4A:
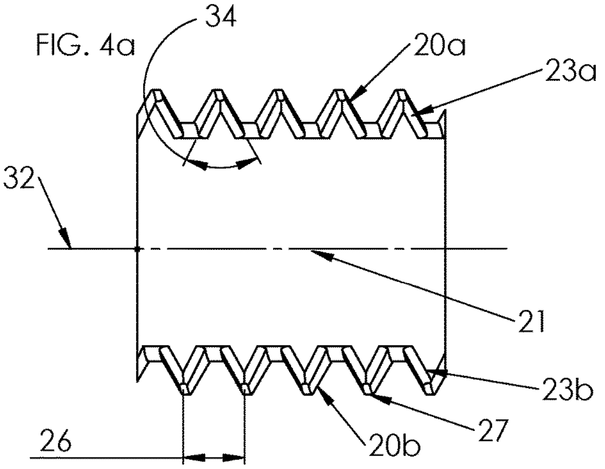
FIG. 4A is a side view of a short section of the plunger configuration illustrated in FIG. 3A.

FIG. 4A illustrates that plunger thread faces 20 can have a thread chamfer 23 at the edge of the plunger threads 66. The thread chamfer 23 can be a fillet and/or a chamfer. The thread chamfer 23 can provide a smooth transition when the plunger thread face 20 engages and/or disengages with the barrel thread face 19. The thread chamfer 23 can provide smoother rotation and/or translation of the plunger 8 with respect to the barrel 5. For example, the thread chamfer 23 can break any sharp edges and/or corners. The thread chamfer 23*a* can be the same or different than the thread chamfer 23*b*. For example, the thread chamfer 23 can offer different engagement with the barrel thread faces 19 when the plunger 8 is rotated in the clockwise direction 29 or in the counter-clockwise with respect to the barrel 5. The thread chamfer 23 can be required for manufacturing (e.g., minimum radius for injection molded parts). A plunger tooth angle 34 can be a standard ANSI, metric and/or acme screw angle. The plunger tooth angle 34 can be a custom angle, a compound angle and/or a curve. A plunger thread pitch 26 can be the same as or different than the barrel thread pitch 38. The plunger thread pitch 26 can be a standard ANSI, metric and/or acme screw angle. The plunger thread pitch 26 can be a custom pitch. The plunger thread pitch 26 can be the distance between two plunger threads 66 on the plunger thread face 20. The lead of the plunger threads 66 and/or the barrel threads 65 can be different than the plunger thread pitch 26 and/or the barrel thread pitch 38. For example, if the plunger threads 66 and/or the barrel threads 65 are formed with two thread starts, then the plunger thread pitch 26 and/or the barrel thread pitch 38 can be half the lead. A plunger thread major profile 27 can be flat, rounded and/or pointed. For example, a flat or rounded plunger thread major profile 27 can impact the engagement with the barrel thread face 19, the barrel 5 and/or the barrel ramp 22. The thread major profile 27 can require minimum radii for manufacturing, such as injection molding. The plunger thread major profile 27 can be rounded, square, rectangular and/or polygonal. The plunger thread pitch 26 and/or the barrel thread pitch 38 can be the same or different than the pitch of the graduation lines 14.

Figure 4B:
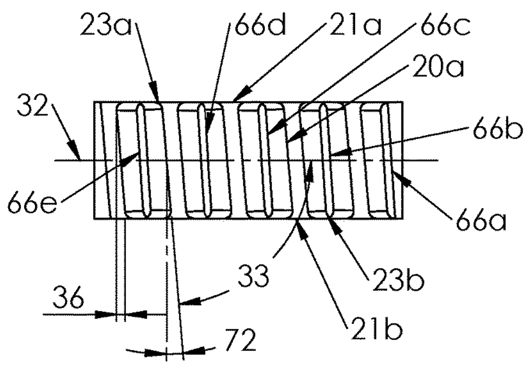
FIG. 4B is the same short section of the plunger illustrated FIG. 4A, but rotated 90 degrees about the longitudinal axis.

FIG. 4B illustrates that the plunger threads 66 on the plunger thread face 20 can have a plunger thread pitch angle 33 with respect to the longitudinal axis 32. The plunger thread face 20 can have one or multiple plunger thread 66. The plunger thread pitch angle 33 can vary over the length of plunger 8. The plunger thread pitch angle 33 can be less than 90 degrees, 90 degrees and/or greater than 90 degrees. A plunger thread complementary angle 72 and the plunger thread pitch angle 33 can be complementary angles. The plunger thread complementary angle 72 can be the angle from the plunger thread 66 to an imaginary line perpendicular to the longitudinal axis 32. A plunger thread longitudinal displacement 36 can impact the distance that the plunger 8 translates with respect to the barrel 5 when the plunger 8 is rotated with respect to the barrel 5. The plunger thread longitudinal displacement 36 can be small enough to allow fine adjustment of the volume of fluid contained in the syringe 1; for example, rotating the plunger 8 in the clockwise direction 29 by 180 degrees with respect to the barrel 5 can translate the fiducial line 12 by approximately one graduation line 14 or approximately one half of the distance between two adjacent graduation lines 14*a* and 14*b*. The barrel thread 65 and/or the plunger thread 66 can be helical. The plunger thread face arc length 77 and/or the plunger thread arc length 35 can be calculated using the plunger thread face arc angle 37, the plunger thread pitch 26, the plunger thread pitch angle 33, the pitch diameter, major diameter and/or minor diameter of the plunger thread(s) 66 in the plunger thread faces 20.

Figure 5:
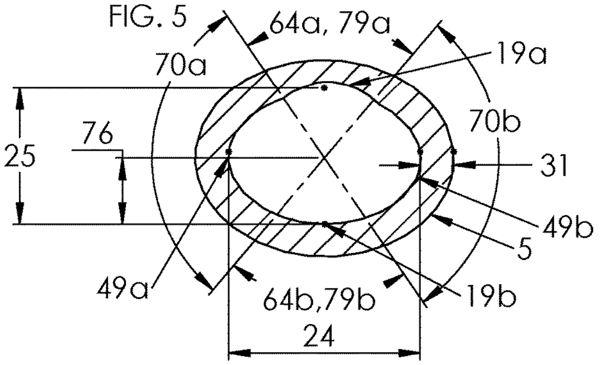
FIG. 5 is a cross-sectional view of the barrel at the barrel engagement region, with the longitudinal axis perpendicular to the page.

FIG. 5 illustrates that the barrel engagement region 50 can have a barrel nut width 24 and a barrel nut height 25. The barrel nut width 24 can be larger, the same and/or smaller than the inside diameter of the barrel 5 in the barrel sealing region 52. The barrel nut height 25 can be larger, the same or smaller than the inside diameter of the barrel 5 in the barrel sealing region 52. The barrel 5 can have a barrel wall thickness 31. The barrel wall thickness 31 can be 0.02 in-0.1 in (0.508-2.54 mm), for example 0.04 in (1.016 mm). The barrel wall thickness 31 can be the same or vary on the barrel 5. The barrel thread face 19*a* and/or 19*b* can be closer to the longitudinal axis 32 than a barrel unthreaded face 49*a* and/or 49*b*. The barrel thread face 19*a* and/or 19*b* can be bounded by a barrel thread face arc angle 64*a* and/or 64*b*, with the vertex of the angle at the longitudinal axis 32. The barrel unthreaded face 49*a* and/or 49*b* can be bounded by a barrel unthreaded face arc angle 70*a* and/or 70*b*, with the vertex of the angle at the longitudinal axis 32. The perimeter of (i.e.

surrounding) the barrel thread face 19 and/or the barrel unthreaded face 49 can be a rectangle, trapezoid, polygon, rhombus, quadrilateral, triangle, parallelogram, circle, oval, oblong and/or any other geometric shape. The perimeter of (i.e. surrounding) the barrel thread face 19 and/or the barrel unthreaded face 49 can be any geometric shape (including but not limited to rectangle, trapezoid, polygonal, triangular, quadrilateral, triangle, oblong, parallelogram, circle and/or oval) wrapped around a cylinder and/or oval (e.g., a rectangle wrapped around the cylindrical barrel 5). The barrel thread face 19 can be a region surrounding all barrel threads 65 that overlap when viewed from the longitudinal axis 32. The barrel thread face 19 can be a quadrilateral wrapped around the barrel 5 that can have two lines perpendicular to the longitudinal axis 32 and two lines parallel to the longitudinal axis 32, wherein the angle between the two parallel lines and the longitudinal axis 32 can be the barrel thread face arc angle 64. The barrel unthreaded face 49 can be the remaining region in the barrel inner surface 68 in the barrel engagement region 50 that is not the barrel thread face 19. The syringe 1 can include the barrel unthreaded face 49 that does not engage with the plunger threads 20. The barrel nut height 25 and/or the barrel nut width 24 can be different when the syringe 1 is in the engaged and/or disengaged configuration. For example, when in the engaged configuration, the plunger thread face 20 can force the barrel thread face 19 radially outwards, thereby increasing the barrel nut height 25 and/or changing the barrel wall thickness 31. There can be several reasons for the plunger thread face 20 to force the barrel thread face 19 radially outwards when in the engaged configuration, including, but not limited to the following: i) to ensure adequate contact between the plunger thread face 20 and the barrel thread face 19 accounting for manufacturing tolerances, environmental factors & aging; ii) to provide an audible sound or tactile feedback when transitioning between engaged and/or disengaged configurations; iii) to increase and/or control the friction between the plunger 8 and the barrel 5; and/or iv) to ensure better longitudinal locking between the plunger 8 and the barrel 5 when in the engaged configuration. The wall of the barrel 5 can be made from a low durometer material, such as silicone, polycarbonate, ABS, Cyclo Olefin Polymer (COP), polyethylene and/or polypropylene. The barrel nut height 25 can be measured from the major, minor, maximum, minimum and/or pitch diameter of the barrel threads 65. The plunger flat width 28 can be less than the barrel nut height 25. The plunger flat width 28 can be configured to never simultaneously contact both sides of the barrel nut height 25 (e.g., both the barrel thread face 19*a* and 19*b*). The barrel 5 can have a barrel thread radial distance 76. The barrel thread radial distance 76 can be constant. The barrel thread radial distance 76 can vary over the length of the barrel 5 and/or over time. The barrel thread radial distance 76 can be the distance from the longitudinal axis 32 to the major, minor, maximum, minimum and/or pitch diameter of the barrel thread face 19. The barrel thread radial distance 76 can be approximately half of the barrel nut height 25 and/or the barrel nut width 24. The barrel thread radial distance 76 can be approximately half of the distance between two opposing barrel thread faces 19*a* and 19*b*. The barrel thread radial distance 76 can be approximately half of the distance between two opposing barrel threads 65*a* and 65*b*.

The wall thickness of the barrel 5, the plunger 8, the plunger stopper 6 and/or the barrel wall thickness 31 can be larger than 0.02 in (0.508 mm), yet more narrowly larger than about 0.03 in (0.762 mm), yet more narrowly larger than about 0.04 in (1.016 mm), yet more narrowly larger than about 0.05 in (1.27 mm), yet more narrowly larger than about 0.06 in (1.524 mm), yet more narrowly larger than about 0.07 in (1.778 mm), yet more narrowly larger than about 0.08 in (2.032 mm) or yet more narrowly larger than about 0.09 in (2.286 mm). The wall thickness of the barrel 5, the plunger 8, the plunger stopper 6 and/or the barrel wall thickness 31 can be smaller than 0.09 in (2.286 mm), yet more narrowly smaller than about 0.08 in (2.032 mm), yet more narrowly smaller than about 0.07 in (1.778 mm), yet more narrowly smaller than about 0.06 in (1.524 mm), yet more narrowly smaller than about 0.05 in (1.27 mm), yet more narrowly smaller than about 0.04 in (1.016 mm), yet more narrowly smaller than about 0.03 in (0.762 mm) or yet more narrowly smaller than about 0.02 in (0.508 mm). The wall thickness of the barrel 5, the plunger 8, the plunger stopper 6 and/or the barrel wall thickness 31 can vary in different locations. The barrel 5 can have a barrel thread arc angle 79. The barrel thread arc angle 79 can be greater, less than or equal to the barrel thread face arc angle 64. For example, the barrel 5 can include different length or angle barrel threads 65*a* and 65*b* on the barrel thread face 19. The barrel thread arc angle 79 can define the arc angle of the barrel thread 65, with the vertex of the angle at the longitudinal axis 32

Figure 6A:
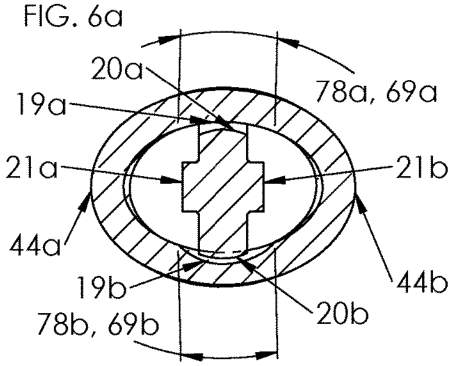
FIG. 6A and FIG. 6B are cross-sectional views of the barrel & plunger at the barrel engagement region and the plunger engagement region, with the longitudinal axis perpendicular to the page.
Figure 6B:
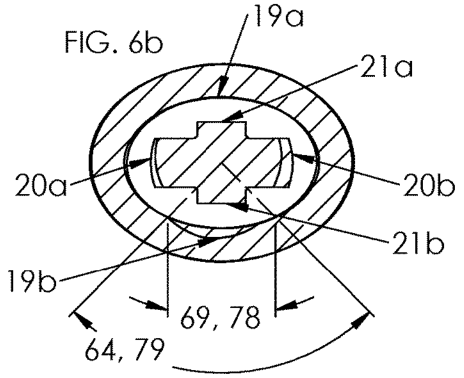

FIG. 6*a* illustrates that the syringe 1 can be in an engaged configuration when the plunger thread face 20 overlaps and/or is in contact with the barrel thread face 19. FIG. 6*b* illustrates that the syringe 1 can be in a disengaged configuration when the plunger thread face 20 is not contacting the barrel thread face 19. The syringe 1 can be in the engaged and/or the disengaged configuration when the plunger thread face 19 is contacting the barrel unthreaded face 49. The syringe 1 can be in the engaged and/or the disengaged configuration when the barrel thread face 20 is contacting the plunger unthreaded face 21. The syringe 1 can transition between the disengaged and the engaged configurations by rotating the plunger 8 with respect to the barrel 5. For example, FIG. 6*a* and FIG. 6*b* illustrates that the plunger 8 can be rotated 90 degrees with respect to the barrel 5 to switch between the disengaged and engaged configurations. The plunger can be rotated greater than or less than 90 degrees with respect to the barrel 5 to transition between the engaged and the disengaged configurations. When rotating the plunger 8 with respect to the barrel 5, approximately half of the total rotational angle (e.g., 360 degrees) can be in the engaged configuration and approximately half can be in the disengaged configuration. The force required to only translate (i.e., without relative rotation) the plunger 8 with respect to the barrel 5 in the disengaged configuration can be less than when the syringe 1 is in the engaged configuration. If the plunger 8 is rotated in the clockwise direction 29 from a disengaged configuration to an engaged configuration to a disengaged configuration, the plunger 8 can translate in the proximal and/or the distal direction 30 by approximately one, two and/or approximately one half of the graduation line 14. If the plunger 8 is rotated in a counter-clockwise direction from a disengaged configuration to an engaged configuration to a disengaged configuration, the plunger 8 can translate in a proximal and/or distal direction by approximately two, one or approximately one half of the graduation line 14. Pushing a barrel squeeze point 44*a* and/or 44*b* towards the longitudinal axis 32 can push the barrel thread face 19 away from the longitudinal axis 32. Pushing the barrel squeeze point 44*a* and/or 44*b* towards the longitudinal axis 32 can cause the syringe 1 to switch between the engaged and/or disengaged configuration. Rotating the plunger 8 in the clockwise direction 29 by 360 degrees with respect to the barrel 5 can switch between engaged and/or disengaged configurations multiple times, such as two, three and/or four times. The barrel thread 65 can have a barrel thread arc length 69 and the barrel thread face 19 can have a barrel thread face arc length 78. The barrel thread arc length 69 and/or the barrel thread face arc length 78 can be the same or different for the barrel thread faces 19*a* and/or 19*b*. The barrel thread arc length 69 can be less than, equal to or greater than the barrel thread face arc length 78. For example, the barrel thread face 19 can have staggered and/or overlapping barrel threads 65. The barrel thread face arc angle 64 can be the maximum angle from one end of the barrel thread 65 to the other end of the barrel thread 65, with the vertex at the longitudinal axis 32. The barrel thread arc face angle 64 can be the maximum angle from one end of the barrel thread face 19 to the other end of the barrel thread face 19, with the vertex at the longitudinal axis 32. The barrel thread arc length 69 can be the three dimensional length of the barrel thread 65 at the major, minor and/or pitch diameter. For example, the barrel thread arc length 69 can be longer for a coarser pitched barrel thread 65 than a shallower pitcher barrel thread 65, even if they have the same barrel thread face arc angle 64. The barrel thread face arc length 78 can be the two dimensional curved length of the barrel thread face 19 at a given cross-section.

Figure 7A:
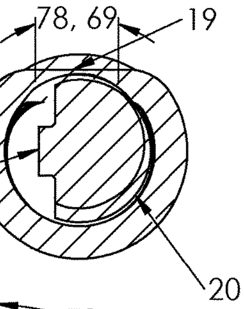
FIG. 7A and FIG. 7B are cross-sectional views of a barrel & plunger at the barrel engagement region and the plunger engagement region, with the longitudinal axis perpendicular to the page.
Figure 7B:
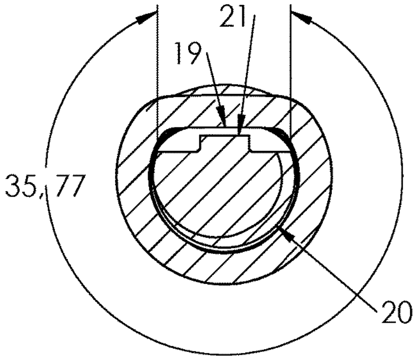

FIG. 7*a* illustrates that the plunger 8 can have one plunger thread face 20 and one plunger unthreaded face 21 in the region of the barrel thread face 19, the plunger engagement region 51 and/or the barrel engagement region 50. Rotating the plunger 8 in the clockwise direction 29 by 360 degrees with respect to the barrel 5 can switch between engaged and/or disengaged configurations multiple times, such as one and/or two times. FIG. 7*a* illustrates the syringe 1 in the engaged configuration and FIG. 7*b* illustrates the syringe 1 in the disengaged configuration.

Figure 8:
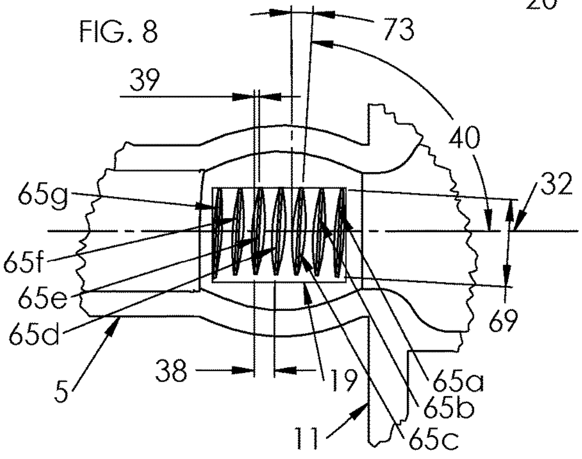
FIG. 8 is a top view of the barrel engagement region of the barrel illustrated in FIG. 2C. The top half of the barrel is removed for illustrative purposes (instead of the left half of the barrel).

FIG. 8 illustrates that the barrel thread face 19 can be comprised of one or multiple barrel threads 65. A barrel thread pitch 38 can be the same pitch as the plunger thread pitch 26. The barrel thread 65 can have one or multiple thread starts. A barrel thread pitch angle 40 can be the same and/or different angle as the plunger thread pitch angle 33. A barrel thread complementary angle 73 and the barrel thread pitch angle 40 can be complementary angles. The barrel thread complementary angle 73 can be the angle from the barrel thread 65 to an imaginary line perpendicular to the longitudinal axis 32. A barrel thread longitudinal displacement 39 can impact the distance that the plunger 8 translates with respect to the barrel 5 when the plunger 8 is rotated with respect to the barrel 5. The plunger thread longitudinal displacement 36, the barrel thread longitudinal displacement 39, the plunger thread pitch angle 33 and/or the barrel thread pitch angle 40 can vary over the length of the plunger 8 and/or the barrel 5. The barrel thread pitch 38 can be the distance between two barrel threads 65. The lead of the barrel threads 65 can be different than the barrel thread pitch 38. For example, if the barrel threads 65 are formed with two thread starts, then the barrel thread pitch 38 can be half the lead. The barrel thread face 19 can be a rectangular region that has all of the barrel threads 65, as illustrated in FIG. 8. The perimeter surrounding the barrel thread face 19 can be rectangular, polygonal, quadrilateral, oblong, circular and/or oval. The barrel thread arc length 69 and/or the barrel thread face arc length 78 can be calculated using the barrel thread face arc angle 64, the barrel thread pitch angle 40, the pitch diameter, major diameter and/or minor diameter of the barrel threads 65 and/or the barrel thread faces 19.

The plunger thread pitch angle 33, the plunger thread face arc angle 37, the barrel thread arc angle 79, the plunger thread arc angle 80, the barrel thread face arc angle 64, the barrel unthreaded face arc angle 70, the plunger unthreaded face arc angle 71, the plunger thread complementary angle 72, the barrel thread complementary angle 73 and/or the barrel thread pitch angle 40 can be larger than about 0 degrees, yet more narrowly larger than about 5 degrees, yet more narrowly larger than about 14 degrees, yet more narrowly larger than about 29 degrees, yet more narrowly larger than about 44 degrees, yet more narrowly larger than about 59 degrees, yet more narrowly larger than 69 degrees, yet more narrowly larger than 74 degrees, yet more narrowly larger than 79 degrees, yet more narrowly larger than 85 degrees, yet more narrowly larger than or yet more narrowly larger than about 104 degrees. The plunger thread pitch angle 33, the plunger thread face arc angle 37, the barrel thread arc angle 79, the plunger thread arc angle 80, the barrel thread face arc angle 64, the barrel unthreaded face arc angle 70, the plunger unthreaded face arc angle 71, the plunger thread complementary angle 72, the barrel thread complementary angle 73 and/or the barrel thread pitch angle 40 can be smaller than about 116 degrees, yet more narrowly smaller than about 91 degrees, yet more narrowly smaller than about 86 degrees, yet more narrowly smaller than about 81 degrees, yet more narrowly smaller than about 76 degrees, yet more narrowly smaller than about 61 degrees, yet more narrowly smaller than about 46 degrees, yet more narrowly smaller than about 31 degrees, yet more narrowly smaller than about 16 degrees, yet more narrowly smaller than about 11 degrees or yet more narrowly smaller than about 6 degrees.

The plunger tooth angle 34 and/or the tooth angle of the barrel threads 65 can be larger than about 0 degrees, yet more narrowly larger than about 14 degrees, yet more narrowly larger than about 29 degrees, yet more narrowly larger than about 44 degrees, yet more narrowly larger than about 59 degrees, yet more narrowly larger than 74 degrees, yet more narrowly larger than 89 degrees, yet more narrowly larger than or yet more narrowly larger than about 104 degrees. The plunger tooth angle 34 and/or the tooth angle of the barrel threads 65 can be smaller than about 116 degrees, yet more narrowly smaller than about 91 degrees, yet more narrowly smaller than about 76 degrees, yet more narrowly smaller than about 61 degrees, yet more narrowly smaller than about 46 degrees, yet more narrowly smaller than about 31 degrees or yet more narrowly smaller than about 16 degrees.

Figure 9A:
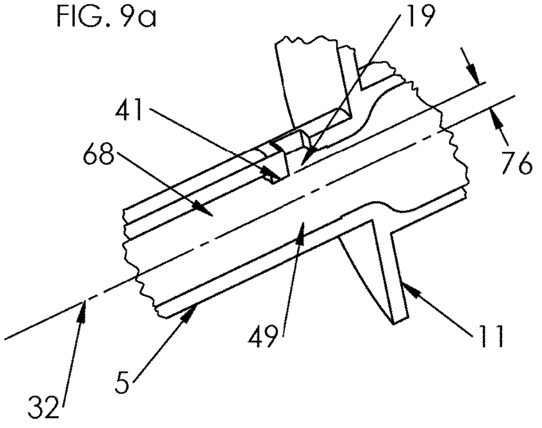
FIG. 9A through FIG. 9D are illustrative isometric views of the barrel engagement region of various barrel designs, with the left half of the barrel removed.
Figure 9B:
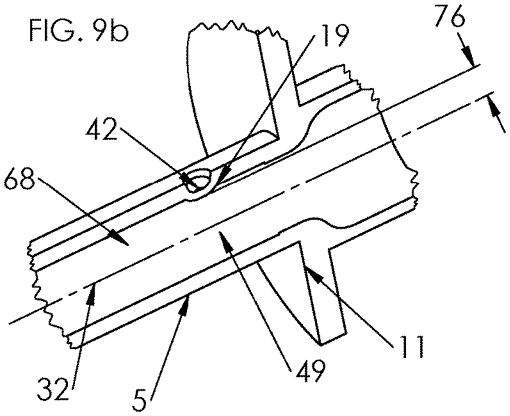
Figure 9C:
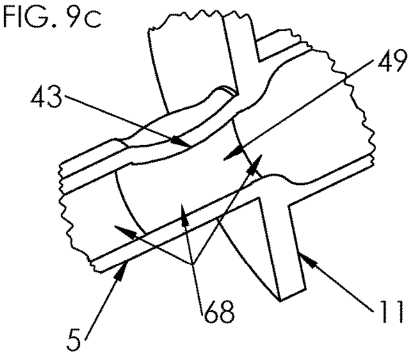
Figure 9D:
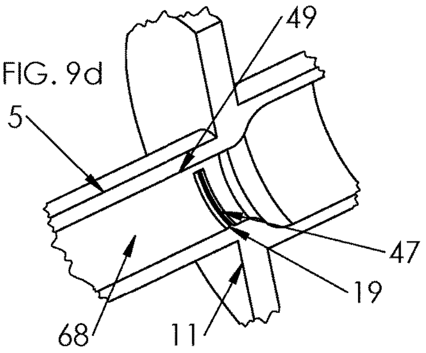

FIG. 9*a* and FIG. 9*b* illustrate that a barrel tab 41 and/or a barrel dimple 42 can be the barrel threads 65 illustrated in FIG. 2. The barrel tab 41 and/or the barrel dimple 42 can not be the barrel threads 65. The barrel tab 41 can be formed by bending and/or deforming a portion of the barrel 5 radially inwards. FIG. 9*c* illustrates that a barrel flat 43 can be closer to the longitudinal axis 32 than the other points along the internal circumference of the barrel 5, the barrel sealing region 52 and/or the barrel engagement region 50. The features and/or the plunger threads 66 on the plunger thread face 20 can form temporary and/or permanent mating features on the barrel flat 43, such as the barrel threads 65. The barrel flat 43 can be made from a softer material than the plunger thread face 20. For example, the threads on the plunger thread face 20 can temporarily and/or permanently form and/or cut threads on the barrel flat 43. FIG. 9*d* illustrates that the barrel 5 can include a barrel bump thread 47. The barrel bump thread 47 can be continuous and/or discontinuous The plunger thread 66 can interact with the barrel tab 41, the barrel dimple 42, the barrel thread 65, the barrel bump thread 47 and/or the barrel threads 65 to translate the plunger 8 with respect to the barrel 5 when the plunger 8 and the barrel 5 are rotated with respect to each other. The barrel tab 41, the barrel thread 65, the barrel dimple 42, the barrel bump thread 47 and/or the barrel flat 43 can be a different component than the barrel 5. The barrel tab 41, the barrel dimple 42, the barrel thread 65, the barrel bump thread 47 and/or the barrel flat 43 can be an integral feature on the barrel 5. The barrel tab 41, the barrel dimple 42, the barrel thread 65, the barrel bump thread 47 and/or the barrel flat 43 can be secured to the barrel 5 with adhesive, a press-fit, a snap-fit, friction, a solvent bond, an ultrasonic weld, a weld, a laser weld, a thread and/or other mechanical means. The barrel tab 41, the barrel thread 65, the barrel dimple 42, the barrel bump thread 47 and/or the barrel flat 43 can be formed during injection molding (e.g., a bump off and/or threaded tooling). The barrel tab 41, the barrel dimple 42, the barrel thread 65, the barrel bump thread 47 and/or the barrel flat 43 can be a feature on the barrel thread face 19 and/or can be the barrel thread face 19. The barrel tab 41, the barrel dimple 42, the barrel thread 65, the barrel bump thread 47 and/or the barrel flat 43 can be integral to the barrel thread face 19. The barrel tab 41, the barrel dimple 42, the barrel thread 65, the barrel bump thread 47 and/or the barrel flat 43 can be rotationally and/or longitudinally fixed to the barrel thread face 19. The barrel tab 41, the barrel dimple 42, the barrel thread 65, the barrel bump thread 47 and/or the barrel flat 43 can be a separate component than the barrel thread face 19. The barrel tab 41, the barrel dimple 42, the barrel thread 65, the barrel bump thread 47 and/or the barrel flat 43 can provide tactile and/or audible feedback as the plunger 8 is rotated with respect to the barrel 5. The barrel tab 41, the barrel dimple 42, the barrel thread 65, the barrel bump thread 47 and/or the barrel flat 43 can provide a small force to lock the syringe 1 in the engaged and/or disengaged configuration.

Figure 10:
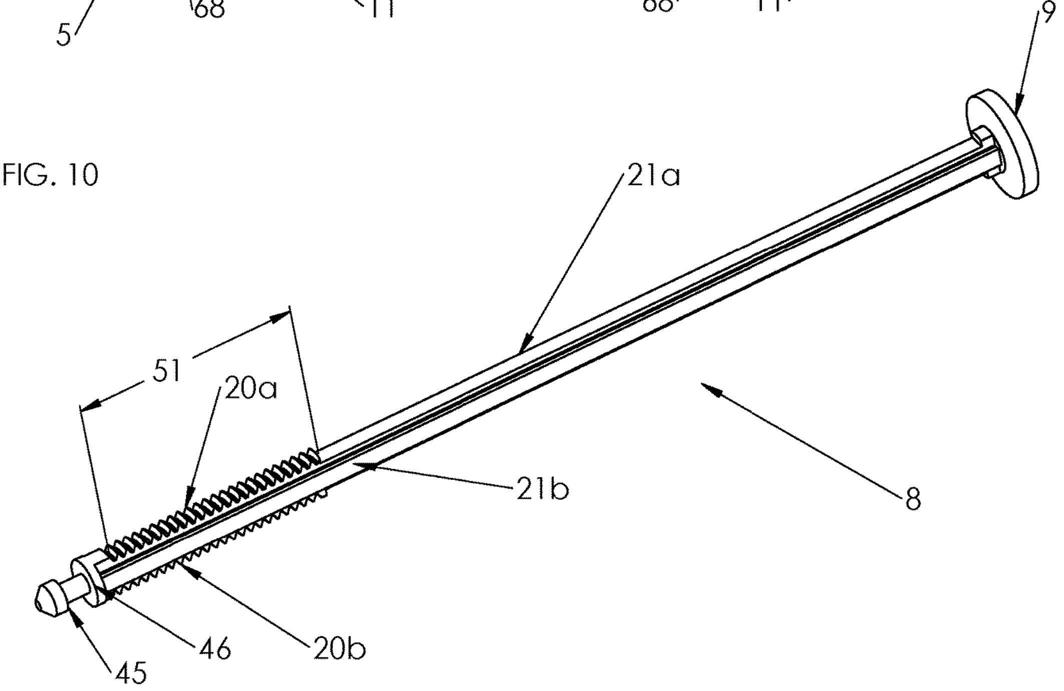
FIG. 10 illustrates the plunger in an isometric view.

FIG. 10 illustrates that the cross-section of the plunger 8 can vary along the length of the plunger 8. A portion of the plunger 8 can not have the plunger thread faces 20 and/or the plunger unthreaded face 21. For example, it can be desirable that a first volume of the syringe 1 can only be in the disengaged configuration and a second volume of the syringe 1 can be in the engaged and/or disengaged configuration. It can be desirable for a first, second, third, or other volume of the syringe 1 to always be in the engaged or disengaged configuration. For example, the syringe 1 can be typically filled to >50% of the total syringe volume (e.g., if a user requires a precise 0.4 mL volume, the user can choose to use a 0.5 mL syringe instead of a 1.0 mL syringe, thereby improving accuracy); therefore, the user can prefer the syringe 1 to be always in the disengaged configuration for volumes less than 50% of the syringe volume. The plunger 8 can include a plunger stopper engagement feature 45 to secure the plunger stopper 6 to the plunger 8. The plunger stopper engagement feature 45 can longitudinally and/or rotationally secure the plunger stopper 6 to the plunger 8. The plunger 8 can include a plunger stop 46 that can help prevent the plunger 8 from being removed from the barrel 5. The plunger stop 46 can allow the seal 7 to maintain a better seal with the barrel 5. The plunger stop 46 can provide support to better constrain the plunger stopper 6. The plunger stop 46 can be a larger, equal and/or smaller diameter than the plunger thread face 20 and/or the plunger unthreaded face 21. The diameter of the plunger stop 46 can be smaller, equal or greater than the major, minor and/or pitch diameter of the plunger thread face 20. The plunger stop 46 can have the plunger thread 66 and/or not have the plunger thread 66.

Figure 11:
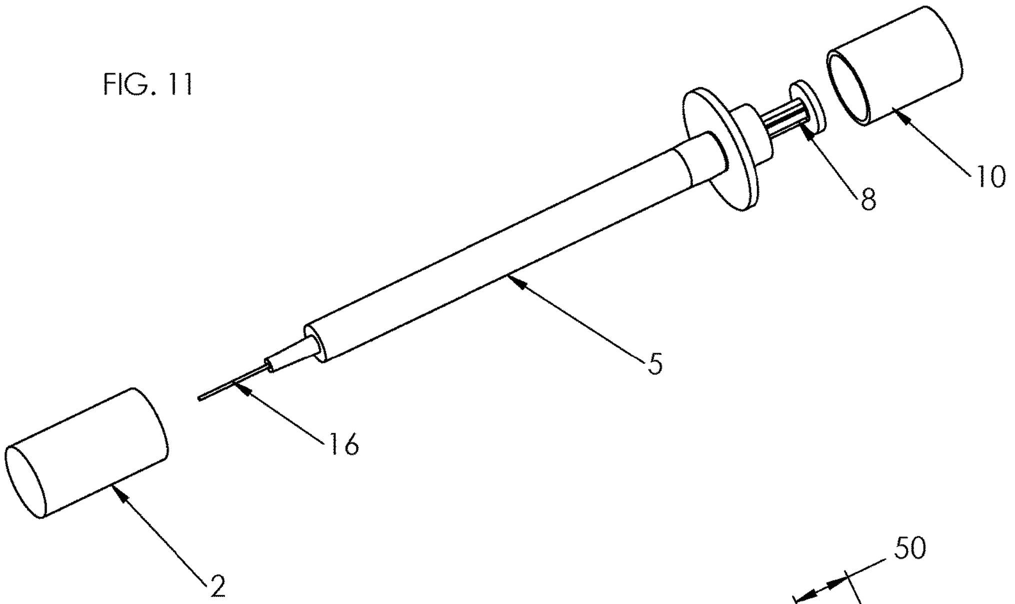
FIG. 11 illustrates the syringe in an isometric view.

FIG. 11 illustrates that the syringe 1 can have a needle tube 16. The needle tube 16 can be a metal tube and/or a polymer tube. The needle tube 16 can be a hypodermic tube and/or needle. The needle tube 16 can have a sharp, blunt and/or beveled end. The tip of the needle tube 16 can be straight, back bevel, franseen, greene point, quincke, hustead, whitacre, short bevel, regular bevel, tuohy, A-bevel, B-bevel, C-bevel, Bias, Chiba, Crawford, Deflected Tip, Francine, Hustead, Huber, Trocar and/or Tuohy. The needle tube 16 can be configured to penetrate through tissue and/or rubber. The needle tube 16 or any component of the syringe 1 can include a lubricant, including but not limited to silicone, teflon and/or mineral oil. The needle tube 16 or any component of the syringe 1 can include a coating, including but not limited to thin film metallic glass, hydrophobic, hydrophilic, teflon, PTFE, ETFE, Parylene and/r silicone. The syringe 1 can have a nozzle cap 2 and/or a plunger cap 10. FIG. 11 illustrates the nozzle cap 2 and the plunger cap 10 disassembled from the barrel 5. The nozzle cap 2 can protect the needle tube 16 from being damaged and/or damaging other objects. For example, the nozzle cap 2 can protect the needle tube 16 from being dented and/or bent. The nozzle cap 2 can prevent the needle tube 16 from puncturing a sterile barrier and/or unintentionally hurting an animal (e.g., a human). The plunger cap 10 can prevent the plunger 8 from unintentionally moving. The plunger cap 10 can maintain the syringe 1 in the engaged and/or the disengaged configuration. The plunger cap 10 can include features to prevent the plunger 8 from translating and/or rotating with respect to the barrel 5. The plunger cap 10 and/or the nozzle cap 2 can provide a sterile and/or clean barrier when assembled to the barrel 5 and/or the plunger 8, ensuring sterility of the fluid path of the syringe 1.

Figure 12A:
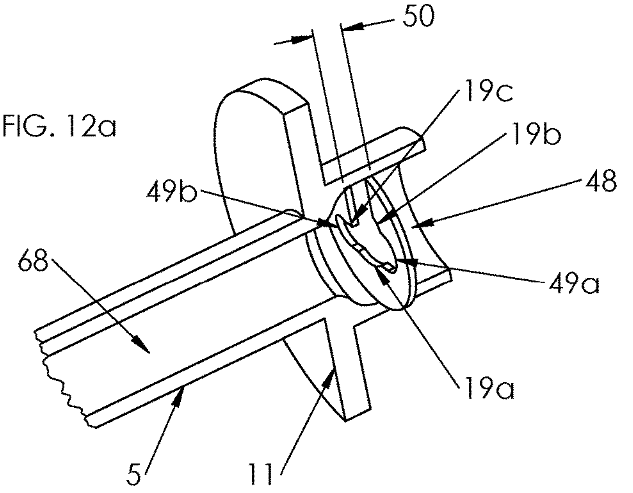
FIG. 12*a* and FIG. 12*b* are illustrative isometric views of the barrel engagement region of various barrel designs, with the left half of the barrel removed.
Figure 12B:
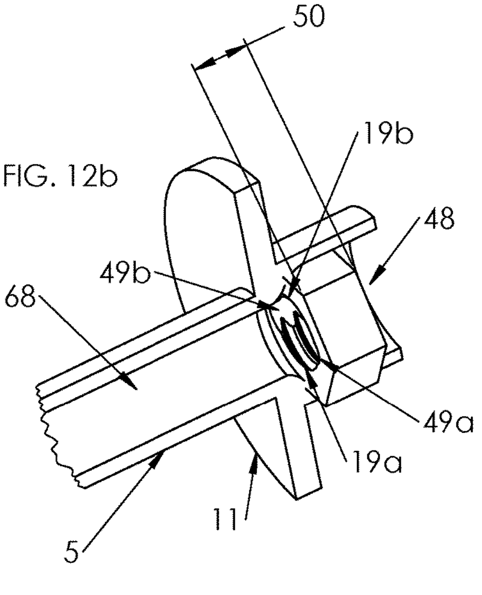

FIG. 12*a* and FIG. 12*b* illustrate that a barrel nut 48 can have the barrel thread face 19 and/or the barrel unthreaded face 49. The barrel nut 48 can include the barrel unthreaded face 49 that can not engage with the plunger thread face 20. The barrel nut 48 can be a separate component and/or the same component as the barrel 5. The barrel nut 48 can be integral with the barrel 5. The barrel nut 48 can be manufactured using a number of different methods including, but not limited to machining, extruding, stamping, laser cutting, injection molding and/or 3D printing. The barrel nut 48 can be designed to press-fit into the proximal end of the barrel 5. The barrel nut 48 can include features to engage with the barrel 5, for example a barb. The barrel nut 48 or any component can be assembled to the syringe 1 using a number of different methods including, but not limited to adhesive, solvent bonding, welding, friction, mechanical means and/or brazing.

The durometer of the barrel nut 48, the barrel thread face 19, the barrel unthreaded face 49, the plunger 8, the barrel 5, the plunger stopper 6, the plunger thread face 20, the plunger unthreaded face 21 and/or any components or features of the syringe 1 can be higher than Shore 00 10, yet more narrowly higher than Shore 00 30, yet more narrowly higher than Shore A 10, yet more narrowly higher than Shore A 30, yet more narrowly higher than Shore A 50, yet more narrowly higher than Shore A 70, yet more narrowly higher than Shore A 90, yet more narrowly higher than Shore D 20, yet more narrowly higher than Shore D 40, yet more narrowly higher than Shore D 60, yet more narrowly higher than Shore D 60 or yet more narrowly higher than Shore D 80. The durometer of the barrel nut 48, the barrel thread face 19, the barrel unthreaded face 49, the plunger 8, the barrel 5, the plunger stopper 6, the plunger thread face 20, the plunger unthreaded face 21 and/or any components or features of the syringe 1 can be less than Shore D 100, yet more narrowly less than Shore D 80, yet more narrowly less than Shore D 60, yet more narrowly less than Shore D 40, yet more narrowly less than Shore D 20, yet more narrowly less than Shore A 90, yet more narrowly less than Shore A 70, yet more narrowly less than Shore A 50, yet more narrowly less than Shore A 30, yet more narrowly less than Shore A 10, yet more narrowly less than Shore 00 30 or yet more narrowly less than Shore 00 10. The durometer of a component can vary in different regions. The barrel thread face 19, the plunger thread face 20 and/or any component of the syringe 1, for example, can include a higher or lower durometer surface than the substrate.

Figure 13:
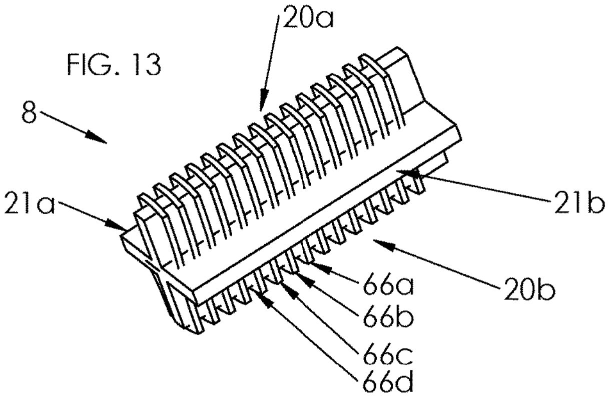
FIG. 13 is an isometric view of a short section of the plunger at the plunger engagement region.

FIG. 13 illustrates a section of the plunger 8 designed for a larger volume syringe (e.g., a 20 mL volume). The plunger threads 66 can extend on multiple surfaces of the plunger 8.

Figure 14A:
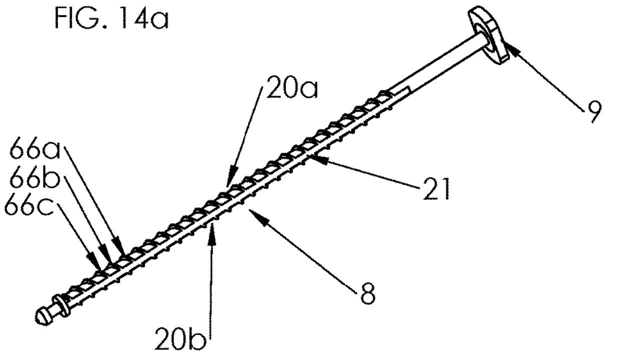
FIG. 14*a* through FIG. 14*d* illustrate the plunger configured to form temporary threads in the barrel nut.
Figure 14B:
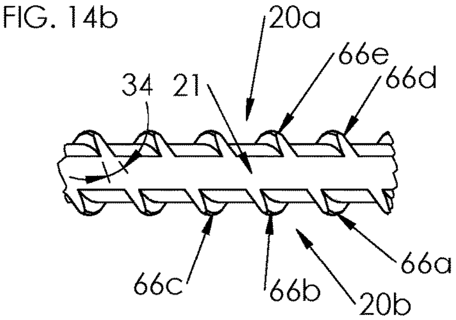
Figure 14C:
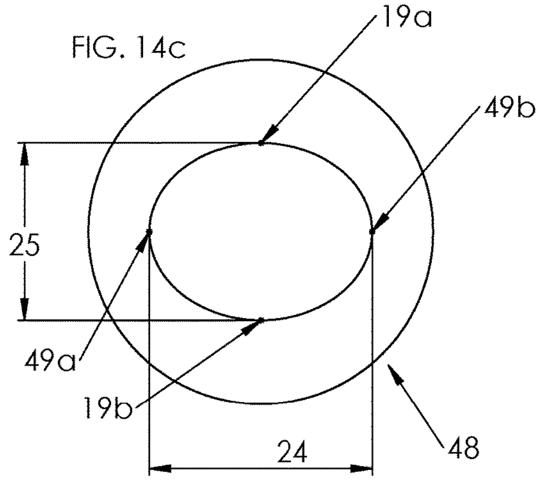
Figure 14D:
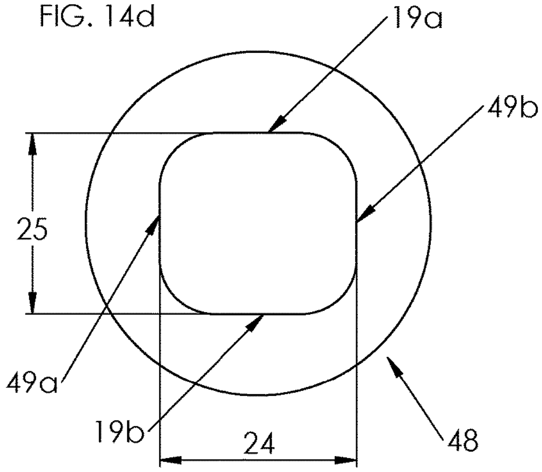

FIG. 14*a* illustrates that the plunger threads 66 can be coarse threads which can be designed to minimize radial and/or circumferential contact with the barrel nut 48, the barrel 5, the barrel flat 43, the barrel thread face 19 and/or the barrel unthreaded face 49. FIG. 14*b* illustrates that plunger tooth angle 34 can be configured to decrease radial contact and/or increase radial pressure when engaged with the barrel nut 48, the barrel 5, the barrel flat 43, the barrel thread face 19 and/or the barrel unthreaded face 49. For example, the plunger threads 66 can form a temporary and/or permanent mating thread on the barrel nut 48, the barrel 5, the barrel flat 43, the barrel thread face 19 and/or the barrel unthreaded face 49. FIG. 14*c* and FIG. 14*d* illustrate that the barrel nut width 24 can be larger, equal to or smaller than the barrel nut height 25. When in the engaged configuration, the plunger thread face 20 can form a temporary and/or permanent mating thread on the barrel thread face 19*a* and/or 19*b*. The barrel thread face 19 can be smooth. The barrel thread face 19 can not have any permanent threads and/or can be manufactured without threads. The entire radially inside surface of the barrel nut 48 can be smooth and/or can be manufactured without threads, tabs, dimples or and/or other features. For example, the barrel nut 48 can be a silicone and/or rubber component. The barrel nut 48 can be an extruded tube. The barrel nut 48 can have a smooth radially internal surface absent of mating features; however, the plunger threads 66 and/or the plunger thread face 20 can contact and deform the barrel thread face 19 such that the plunger 8 can translate relative to the barrel nut 48 when they are rotated with respect to each other.

Figure 15:
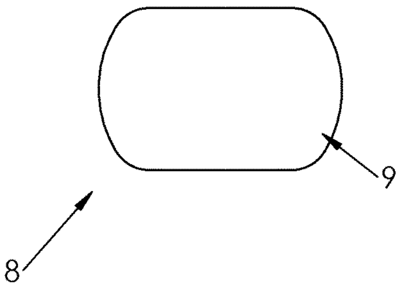
FIG. 15 illustrates a cross-sectional view of a plunger push button, with the longitudinal axis perpendicular to the page.

FIG. 15 illustrates that the push button 9 can be configured to provide a visual guide for the orientation of the plunger 8. The push button 9 and/or the barrel flange 11 can be configured to provide improved grip when rotating and/or translating the plunger 8 and/or the barrel 5. For example, the push button 9 and/or the barrel flange 11 can be various shapes, including but not limited to circular, oblong, oval, rectangular, triangular, polygonal, diamond shape, “T” shaped, “+” shaped and/or ellipse shaped. The push button 9 can have knurls and/or teeth along the outside surface to provide improved grip when rotating the plunger 8. The barrel flange 11, a radially external surface of the barrel 5 and/or a radially external surface of the plunger 8 can have knurls and/or teeth to provide improved grip when rotating. The push button 9 and the flange 11 can have and/or be of similar cross-sections and/or external shapes. For example, the push button 9 and the flange 11 can both be shaped similarly to the shape illustrated in FIG. 15. When the shapes on the push button 9 and the flange 11 are both approximately aligned with each other when viewed from the proximal end of the syringe 1, the syringe 1 can be in the disengaged configuration and/or the engaged configuration. When the shapes on the push button 9 and the flange 11 are both approximately perpendicular to each other when viewed from the proximal end of the syringe 1, the syringe 1 can be in the disengaged configuration and/or the engaged configuration.

Figure 16A:
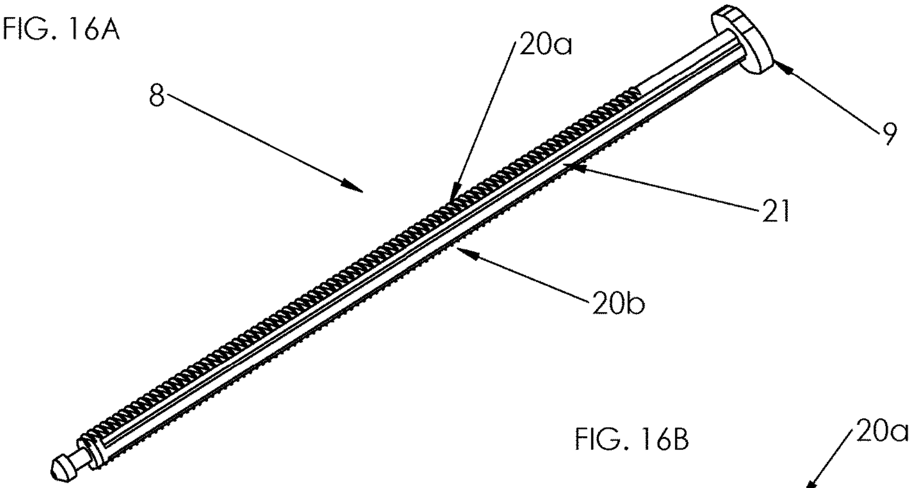
FIG. 16*a* through FIG. 16*d* illustrate the plunger.
Figure 16B:
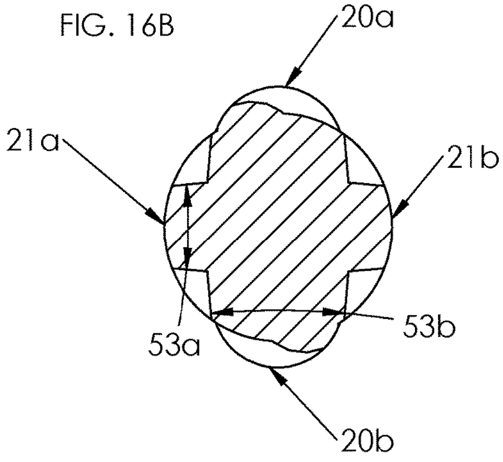
Figure 16C:
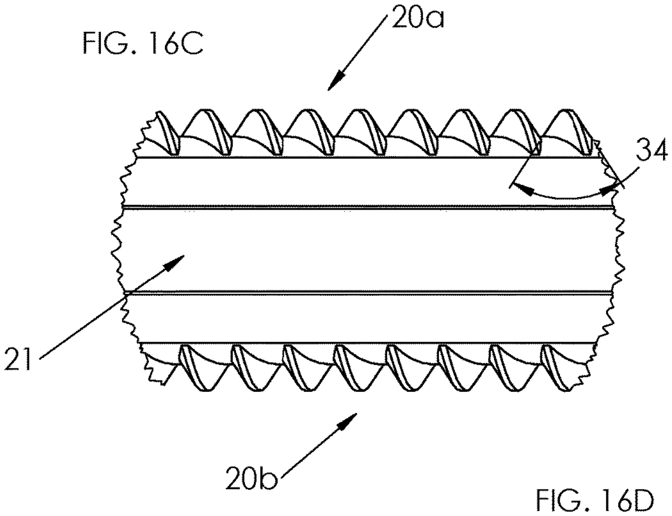
Figure 16D:
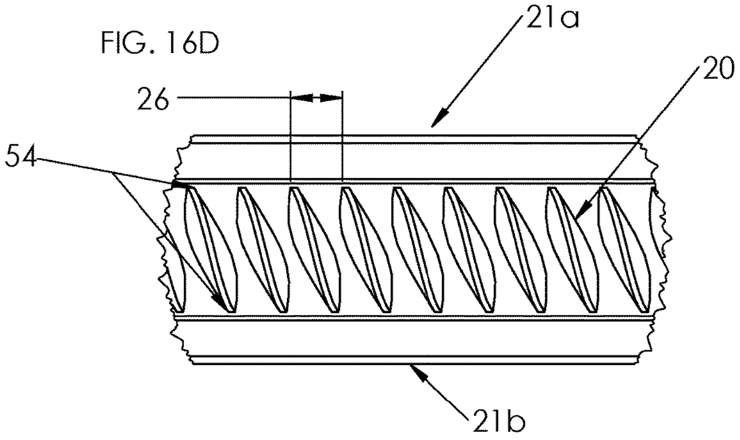

FIG. 16*a* illustrates that the plunger 8 can have an ovalized, oblong and/or non-circular push button 9, similar to that shown in FIG. 15. The plunger 8 can have a non-circular cross-section. For example, the plunger 8 can have material removed to reduce the total material in the component, provide an improved user grip and/or for improved injection molding. FIG. 16*b* illustrates that the plunger 8 can have a plunger draft 53*a* and/or 53*b*. The plunger draft 53 can be beneficial for improved manufacturing (e.g., injection molding). The plunger draft 53 and/or other draft in the syringe 1 can be larger than 0 degrees, yet more narrowly larger than approximately 5 degrees, yet more narrowly larger than approximately 15 degrees or yet more narrowly larger than approximately 30 degrees. The plunger draft 53 and/or other draft in the syringe 1 can be less than approximately 60 degrees, yet more narrowly less than approximately 30 degrees, yet more narrowly less than approximately 10 degrees, yet more narrowly less than approximately 6 degrees or yet more narrowly less than approximately 3 degrees. The barrel threads 65 and/or the plunger threads 66 can be rounded. Rounded threads on the plunger thread face 20 can allow for smoother and/or better engagement with threads and/or mating features on the barrel 5, the barrel nut 48 and/or barrel thread face 19. FIG. 15*c* and FIG. 16*d* illustrate that the plunger threads 66 on the plunger thread face 20 can have a non-concentric major diameter with respect to the longitudinal axis 32 and/or the plunger 8. The diameter of the plunger threads 66 can vary over the length of the plunger thread 66. The plunger threads 66 can be non-circular; for example, they can be oval and/or various curved profiles. A thread end 54 can or can not contact the barrel threads 65, mating features on the barrel 5, the barrel nut 48 and/or barrel thread face 19. The thread end 54 can allow a smooth transition to engage with the barrel thread face 19. The thread end 54 can be and/or function similarly to the thread chamfer 23.

Any threads on the plunger 8 and/or the barrel 5 can be a spring, coil and/or wire form secured to the plunger 8 and/or the barrel 5. The plunger threads 66 and/or the barrel threads 65 can be a spring, coil and/or wire form secured to the plunger 8 and/or the barrel 5. The barrel 5 and/or the plunger 8 can have features to prevent or provide feedback at certain rotational angles; for example, tactile, visual and/or auditory feedback can be provided when in or transferring between the engaged and/or the disengaged configuration. The barrel nut 48 can have the barrel ramp 22. The barrel tab 41, the barrel dimple 42, the barrel bump thread 47, the barrel flat 43, the barrel nut 48 and/or the barrel 5 can all have the barrel thread face 19. The barrel thread face 19 can have the barrel ramp 22, the thread chamfer 23, the barrel nut width 24, the barrel nut height 25, the barrel thread pitch 38, the barrel thread longitudinal displacement 39, the barrel thread pitch angle 40, the barrel unthreaded face 49, the barrel engagement region 50, the barrel sealing region 52 and/or the barrel squeeze points 44.

Figure 17A:
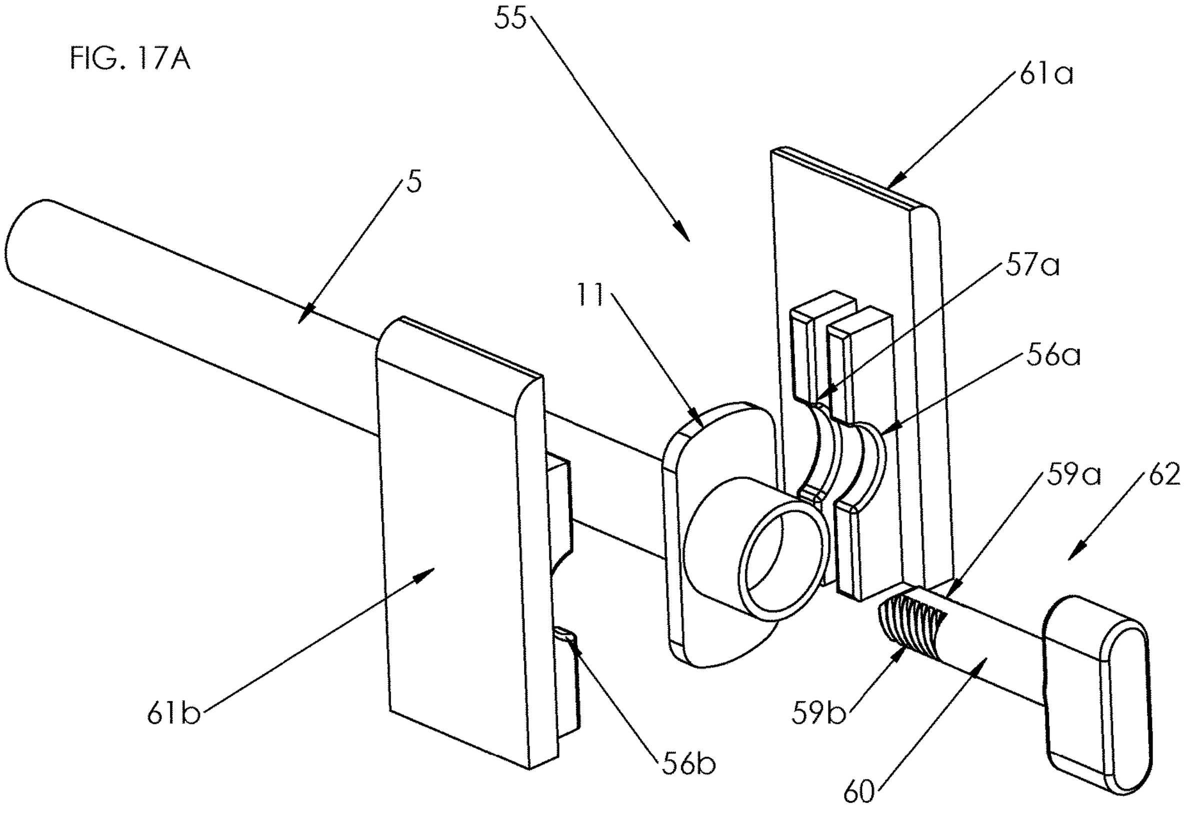
FIG. 17*a* is an illustrative isometric view of a tool for forming the barrel threads and/or the barrel thread face.
Figure 17B:
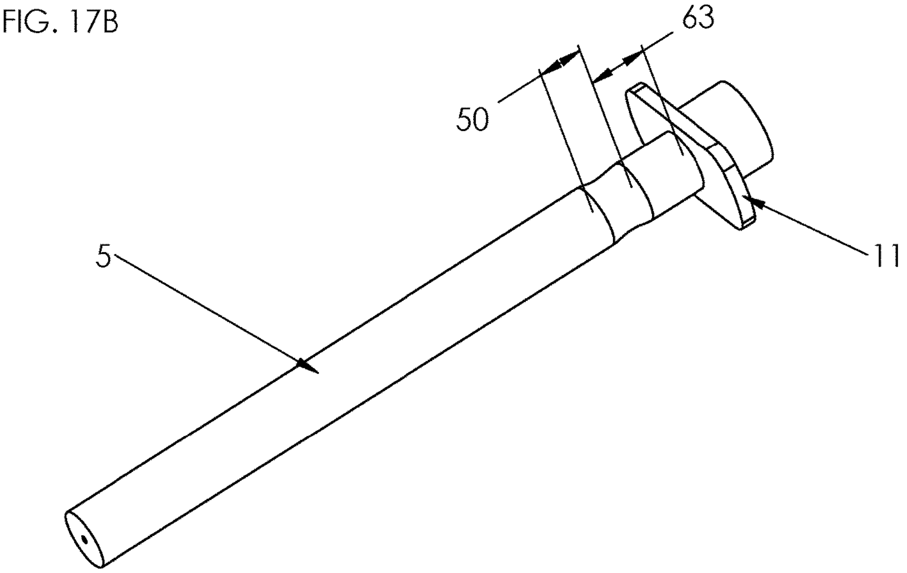
FIG. 17*b* is an illustrative isometric view of the barrel after the barrel thread face(s) has been formed.

FIG. 17*a* illustrates that a barrel thread forming tool 55 can be used to form the barrel thread face 19. The barrel thread forming tool 55 can include an external clamp 61*a* and/or 61*b*. There can be one or multiple external clamp 61. The external clamp 61*a* can be a mirror image of the external clamp 61*b* and/or have mirrored features. The barrel thread forming tool 55 can include an internal thread form tool 62. The barrel thread forming tool 55 can be a metal (such as stainless steel, aluminum, anodized aluminum, steel, copper and/or brass), a ceramic, a natural material (e.g., stone and/or wood) and/or a polymer. The syringe 1, the barrel 5, the external clamp 61 and/or the internal thread form tool 62 can be heated and/or cooled. Portions of the syringe 1, the barrel 5, the external clamp 61 and/or the internal thread form tool 62 can be heated and/or cooled. A portion of the barrel 5 can be heated and/or cooled. For example, the barrel engagement region 50 can be heated while the remainder of the barrel 5 can be cooled. The syringe 1, the barrel 5, the external clamp 61 and/or the internal thread form tool 62 can be heated and/or cooled at different time periods. For example, the barrel engagement region 50 can be heated and then cooled. The internal thread form tool 62 can be inserted into the proximal end of the barrel 5. The external clamp 61*a* and 61*b* can compress the barrel 5 over the internal thread form tool 62. An external thread form 57*a* and/or 57*b* can compress the barrel 5 over an internal thread form 59*a* and/or 59*b*. The external thread form 57 and/or the internal thread form 59 can have a non-circular cross-section. For example, the external thread form 57 and/or the internal thread form 59 can have a cross-sectional profile similar to that shown in FIG. 5. An external non-thread form 56*a* and/or 56*b* can compress and/or constrain the barrel 5 over an internal non-thread form 60. For example, the cross-section of the external non-thread form 56 and/or the internal non-thread form 60 can have a circular cross-sectional profile that can be a clearance and/or tight fit with the barrel 5. The external non-thread form 56 and/or the internal non-thread form 60 can maintain the original cross-section of the barrel 5 while the barrel engagement region 50 is formed. The barrel thread forming tool can not have the external non-thread form 56. The external thread form 57, the external non-thread form 56, the internal non-thread form 60 and/or the internal thread form 59 can be smooth. The external thread form 57, the external non-thread form 56 and/or the internal non-thread form 60 can have features included on the internal thread form 59. For example, if the internal thread form 59 has threads, then the external thread form 57 can be smooth and/or have threads. Any threads on the internal thread form 59 and the external thread form 57 can have the same and/or different pitch, lead, angle and/or profile. The cross-sectional profile of the internal thread form 59 and/or the external thread form 57 can be round, polygonal, triangular, oblong, oval, rectangular and or quadrilateral. The profile of the external thread form 57*a* can be approximately half of the profile of the internal thread form 59. For example, if the internal thread form 59 is a circle, then the external thread form 57*a* and/or 57*b* can be a semicircle and/or less than half of a circle. For example, if the internal thread form 59 is an oval, then the external thread form 57*a* and/or 57*b* can be a semi-oval and/or less than half of an oval. When the external thread form 57*a* and/or 57*b* clamp around the barrel 5, they can form a profile that is an approximate offset of the internal thread form 59; the offset can be approximately equal to the barrel wall thickness 31. The internal thread form 59 and/or the internal non-thread form 60 can be threaded circular rod having multiple thread starts. For example, the internal thread form 59 and/or the non-thread form 60 can have two thread starts with a lead of approximately 0.08-0.12 inches (2-3 mm). For example, the internal thread form 59 and/or the non-thread form 60 can have three thread starts with a lead of approximately 0.12-0.16 inches (3-4 mm). The pitch between threads on the internal thread form 59 can be approximately equal to twice the distance between two adjacent graduation lines 14. The entire outside of the internal thread form 59 and/or the non-thread form 60 can be threaded. FIG. 17*b* illustrates that the barrel engagement region 50 can be separated from the barrel flange 11 by a proximal barrel section 63. The proximal barrel section 63 can be a circular and/or an unformed section of the barrel 5. The proximal barrel section 63 can be a zone transitioning from the barrel engagement region 50 to the barrel sealing region 52. The section distal to the barrel engagement region 50 can be a circular and/or an unformed section of the barrel 5. The proximal barrel section 63 can be distal to the barrel engagement region 50. The proximal barrel section 63 can provide support for the plunger 8 when the plunger 8 is translated and/or rotated with respect to the barrel 5. The proximal barrel section 63 can be circular. The proximal barrel section 63 can include a feature that can provide a tactile and/or audible signal when the plunger 8 is rotated with respect to the barrel 5, such as the barrel tab 41, the barrel dimple 42, the barrel thread 65, the barrel bump thread 47 and/or the barrel flat 43. The external clamp 61 can have the external non-thread form 56 proximal and/or distal to the external thread form 57. The internal thread form tool 62 can have the internal non-thread form 60 proximal and/or distal to the internal thread form 59. The external thread form 57, the external non-thread form 56, the internal non-thread form 60, the barrel 5, the internal thread form 59 and/or any regions of the syringe 1 and/or the barrel thread forming tool 55 can be heated and/or cooled at different temperatures than each other. The external thread form 57, the external non-thread form 56, the internal non-thread form 60, the barrel 5, the internal thread form 59 and/or any regions of the syringe 1 and/or the barrel thread forming tool 55 can be heated and/or cooled at different times than each other.

Figure 18A:
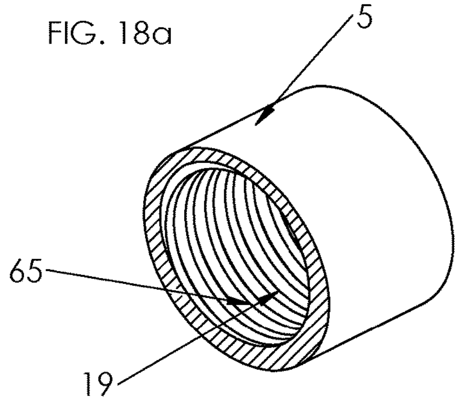
FIG. 18*a* through FIG. 18*d* illustrate short sections of the barrel engagement region and the plunger engagement region of a fully threaded syringe in an isometric view.
Figure 18B:
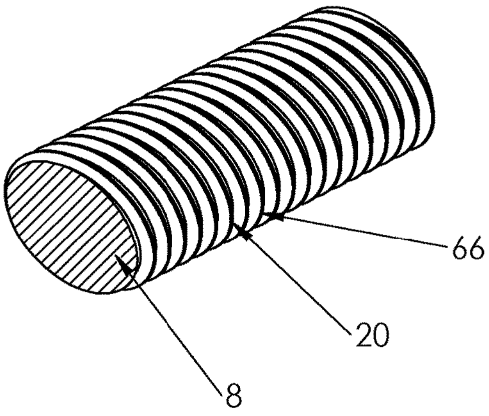
Figure 18C:
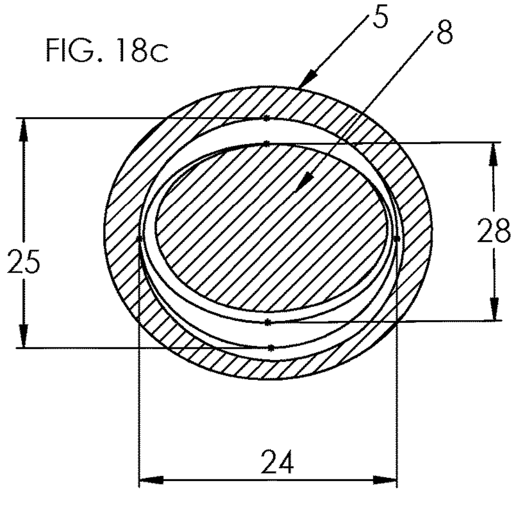
Figure 18D:
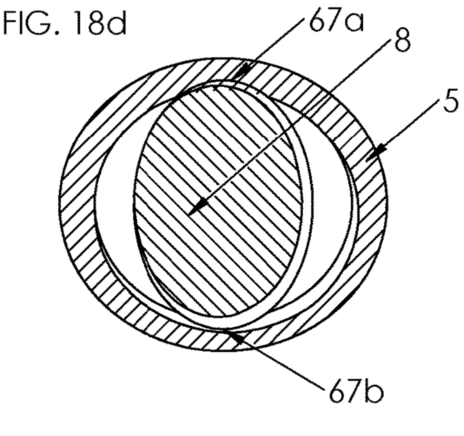

FIG. 18*a* through FIG. 18*d* illustrate that the barrel threads 65 and/or the plunger threads 66 can be continuous. FIG. 18*a* illustrates that the barrel threads 65 can be continuous for part or all of the inner surface of the barrel engagement region 50 and/or the barrel inner surface 68. The cross-section of the barrel engagement region 50 can be ovalized so that the radial distance from the longitudinal axis 32 to the barrel thread 65 can vary over the circumference of the barrel 5. FIG. 18*b* illustrates that the plunger threads 66 can be continuous at part or all of the outer surface of the plunger engagement region 51 and/or the outer surface of the plunger 8. The cross-section of the plunger engagement region 51 can be ovalized so that the radial distance from the longitudinal axis 32 to the plunger thread 66 can vary over the circumference of the plunger 8. FIG. 18*c* illustrates that in the disengaged configuration, the plunger threads 66 can not engage with the barrel threads 65. In the disengaged configuration, only one portion of the plunger threads 66 can engage with the barrel threads 65; for example, one edge side, region and/or edge of the plunger 8 can engage with the barrel 5 while the opposite side, region and/or edge can not be in contact. When in the disengaged configuration, if the plunger 8 and the barrel 5 are concentric and/or coaxial, they can not be in contact in the barrel engagement region 50. The barrel thread 65 and/or the plunger thread 66 can be formed while the barrel 5 and/or the plunger 8 have a round (e.g. circular) profile and then the barrel 5 and/or the plunger 8 can be ovalized temporarily and/or permanently. FIG. 18*d* illustrates that when the plunger 8 is rotated 90 degrees with respect to the barrel 5 (from the orientation shown in FIG.

18*c*), the syringe 1 can be in the engaged configuration. In the engaged configuration, two sides, edges and/or regions of the plunger 8 can be in contact with the barrel 5. In the engaged configuration, one and/or multiple sides, edges and/or regions of the plunger 8 can be in contact with the barrel 5. For example, the plunger 8 can contact the barrel 5 in a contact region 67*a* and/or 67*b* when in the engaged configuration.

Figure 19:
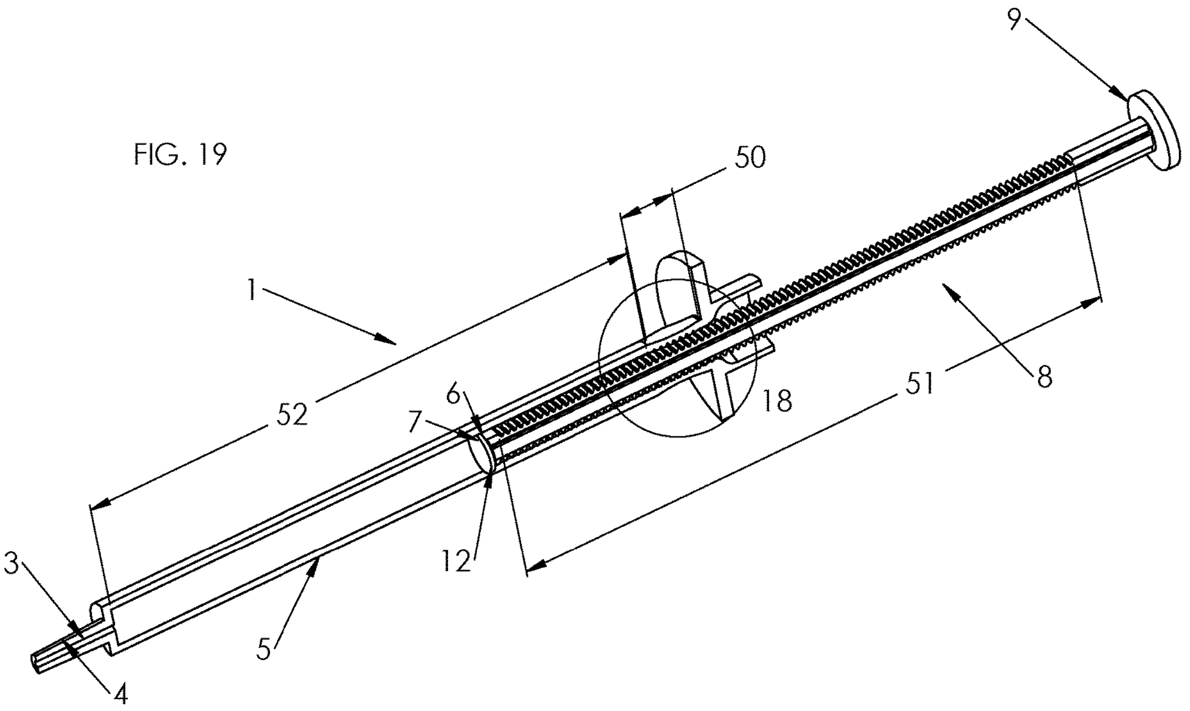
FIG. 19 is an illustrative isometric view of a two piece syringe with a left half of the barrel removed.

FIG. 19 illustrates that the plunger stopper 6 can be integral with the plunger 8. For example, the plunger stopper 6 can be part of the plunger 8. The syringe 1 can be a two piece syringe, with the seal 7 integral with the plunger 8.

Figure 20:
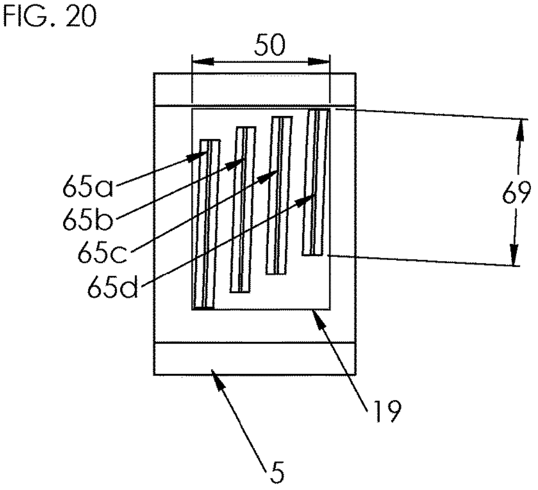
FIG. 20 is a top view of the barrel engagement region of the barrel with the top half of the barrel removed.

FIG. 20 illustrates that the barrel threads 65 can be staggered and/or overlap. For example, the barrel threads 65 can be modeled as a curve driven pattern, a linear pattern, a helical and/or a non-linear pattern. The barrel thread face 19 and/or the perimeter of the barrel thread face 19 can be a rectangle and/or rhombus wrapped around the inside of the barrel 5 that fully encompasses all of the barrel threads 65. The plunger threads 66 can be modeled as a curve driven pattern, a linear pattern, a helical and/or a non-linear pattern similar to the barrel threads 65. The plunger threads 66 and/or the barrel threads can vary over the length of the syringe 1. For example, the barrel thread arc length 69, the barrel thread face arc length 78, the plunger thread arc length 35 and/or the plunger thread face arc length 77 can vary at different regions of the syringe 1.

Figure 21A:
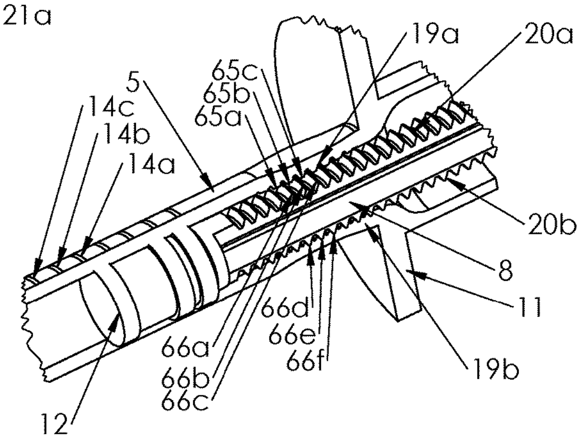
FIG. 21*a* through FIG. 21*i* are illustrative isometric views of a proximal section of the syringe with a left half of the barrel removed.
Figure 21B:
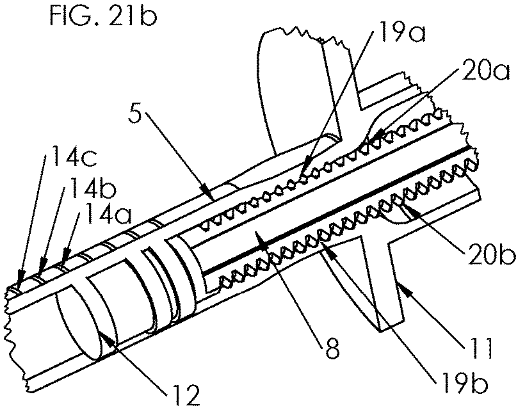
Figure 21C:
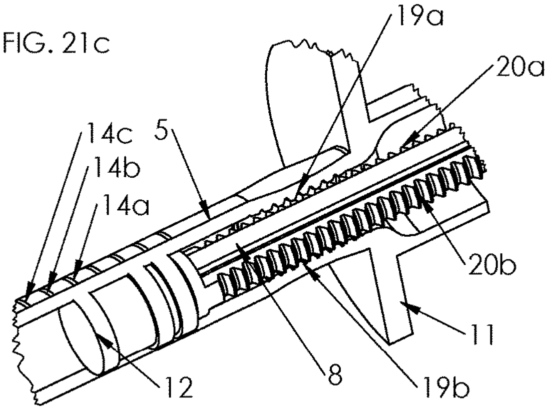
Figure 21D:
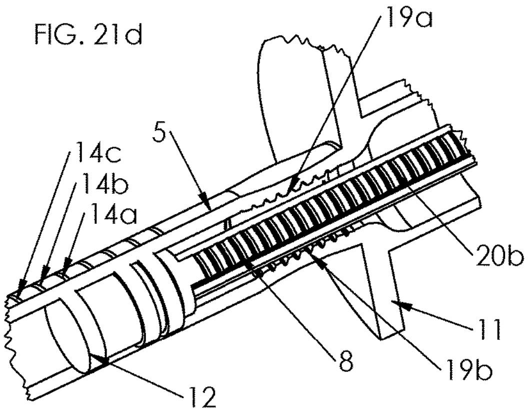
Figure 21E:
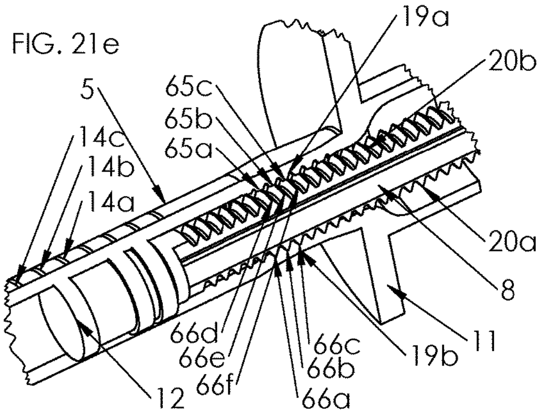
Figure 21F:
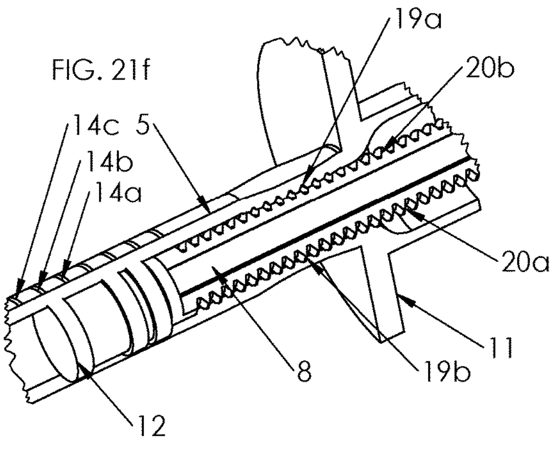
Figure 21G:
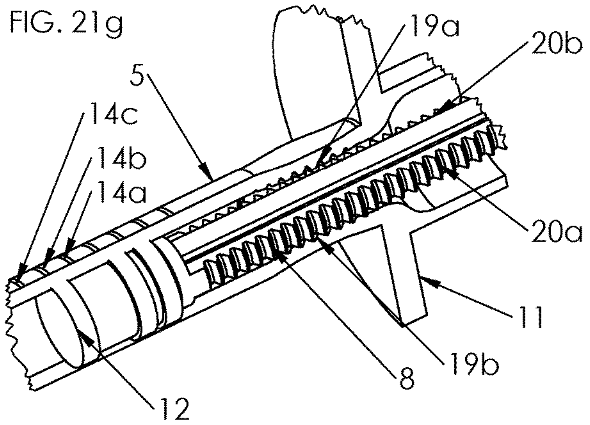
Figure 21H:
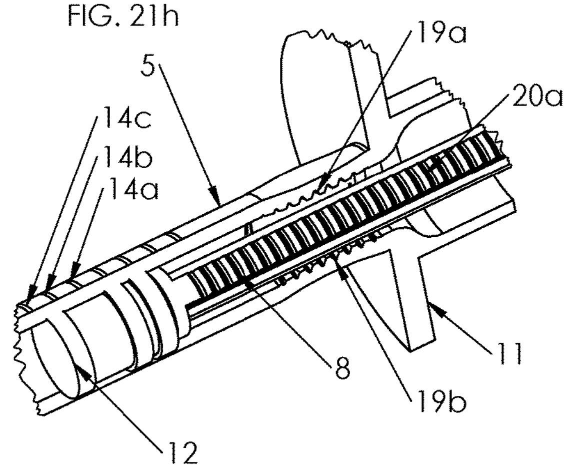
Figure 21I:
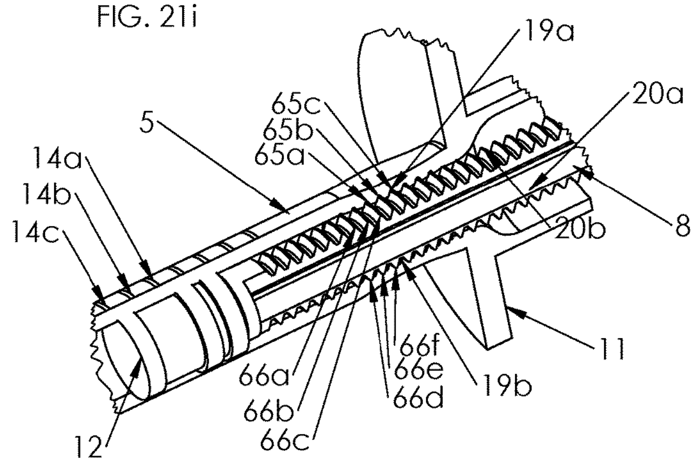

FIG. 21*a* illustrates the syringe 1 in the engaged configuration, with the fiducial line 12 at approximately the graduation line 14*a*. In the engaged configuration, the plunger thread faces 20*a* and/or 20*b* can be engaged and/or locked with the barrel thread faces 19*a* and/or 19*b*. In the engaged configuration, the volume of fluid contained within syringe 1 can not be adjusted significantly without rotating the plunger 8 with respect to the barrel 5. FIG. 21*b* illustrates the plunger 8 rotated 45 degrees in the clockwise direction 29 with respect to the plunger 8 position illustrated in FIG. 21*a*. Depending on the barrel thread face arc angle 64 and the plunger thread face arc angle 37, the syringe 1 can be in the engaged and/or disengaged configuration. For example, if the syringe 1 has two equal plunger thread faces 20 and two equal barrel thread faces 19, and if the plunger thread face 20 is centered with respect to the barrel thread face 19 (i.e., the syringe 1 is in the engaged configuration), then the plunger 8 must rotate at least the following amount with respect to the barrel 5 to be in the disengaged configuration: the average distance of the plunger thread face arc angle 37 and the barrel thread face arc angle 64 (i.e. the sum of the plunger thread face arc angle 37 and the barrel thread face arc angle 64, divided by two). For example, if the syringe 1 has two equal plunger thread faces 20 with the plunger thread face arc angle 37 equal to 25 degrees and two equal barrel thread faces 19 with the barrel thread face arc angle 64 equal to 20 degrees, then the syringe 1 can be in the engaged configuration for approximately 45 degrees per 180 degrees of rotation and in the disengaged configuration for approximately 135 degrees per 180 degrees of rotation. When the plunger 8 is rotated with respect to the barrel 5 in the engaged configuration, the plunger 8 can longitudinally translate with respect to the barrel 5. FIG. 21*c* illustrates the plunger 8 rotated 45 degrees in the clockwise direction 29 with respect to the plunger 8 position illustrated in FIG. 21*b*. FIG. 21*c* illustrates that the syringe 1 can be in the disengaged configuration when the plunger thread face 20 is not in contact with the barrel thread face 19. In the disengaged configuration, the plunger 8 can be translated longitudinally with respect to the barrel 5 with or without rotating the plunger 8 with respect to the barrel 5. FIG. 21*d* through FIG. 21*i* illustrate the plunger 8 rotating with respect to the barrel 5 an additional 45 degrees per figure. FIG. 21*e* illustrates the plunger 8 rotating 180 degrees with respect to the orientation of the plunger 8 illustrated in FIG. 21*a*. FIG. 21*i* illustrates the plunger 8 rotating 360 degrees with respect to the orientation of the plunger 8 illustrated in FIG. 21*a*. FIG. 21*a* through FIG. 21*e* illustrate that rotating the plunger 8 with respect to the barrel 5 can advance the plunger 8 with respect to the barrel 5. For example, compared to the starting position in FIG. 21*a*, FIG. 21*e* illustrates that the plunger 8 and/or the fiducial line 12 can advance from the graduation line 14*a* to the graduation line 14*b*. For example, compared to the starting position in FIG. 21*a*, FIG. 21*i* illustrates that the plunger 8 and/or the fiducial line 12 can advance from the graduation line 14*a* to the graduation line 14*c*. The translation of the plunger 8 and/or the fiducial line 12 with respect to the barrel 5 can be caused by rotating the plunger 8 with respect to the barrel 5. The plunger 8 can continue to translate with respect to the barrel 5 by rotating the plunger 8 with respect to the barrel 5, repeating the same steps illustrated in FIG. 21*a* through FIG. 21*i*. The plunger 8 can be rotated in the counterclockwise direction (e.g., a direction opposite the clockwise direction 29) relative to the barrel 5, as illustrated in the reverse sequence of FIG. 21 (e.g., FIG. 21*i* through FIG. 21*a*). If the plunger 8 is rotated in the counterclockwise direction relative to the barrel 5, the plunger 8 can translate from the graduation line 14*c* to the graduation line 14*a*.

Figure 22A:
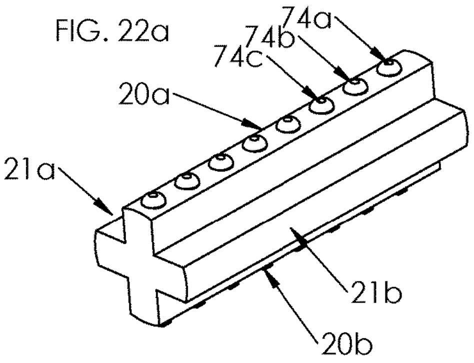
FIG. 22*a* and FIG. 22*b* are illustrative isometric views of a short section of the plunger.
Figure 22B:
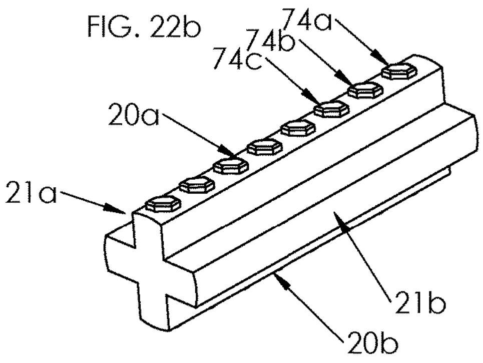

FIG. 22*a* and FIG. 22*b* illustrate that the plunger thread face 20 can include features that can engage with the features on the barrel thread face 19. For example, the plunger bumps 74 can engage with the barrel thread 65, the barrel thread face 19, the barrel tab 41, the barrel dimple 42 and/or the barrel flat 43. The plunger bumps 74 can be the plunger threads 66. The plunger bumps 74 and/or the plunger threads 66 can threadedly engage with the barrel thread 65, the barrel thread 19, the barrel tab 41, the barrel dimple 42 and/or the barrel flat 43. The plunger bumps 74 and/or the plunger threads 66 can helically engage with the barrel thread 65, the barrel thread 19, the barrel tab 41, the barrel dimple 42 and/or the barrel flat 43. The plunger bumps 74 can be bosses and/or dimples. The plunger bumps 74 can be circular, oval, rectangular, quadrilateral, polygon, triangular, rectilinear, trapezoidal, rhombus and/or any other geometric shape. FIG. 22*a* illustrates circular plunger bumps 74 and FIG. 22*b* illustrates polygonal plunger bumps 74.

The plunger 8 can rotate with respect to the barrel 5 greater than 180 degrees, yet more narrowly greater than 360 degrees, yet more narrowly greater than 720 degrees, yet more narrowly greater than 3600 degrees, yet more narrowly an infinite number of times. The maximum number of degrees that the plunger 8 can rotate with respect to the barrel 5 can be limited by the number of graduation lines 14 and the advancement of the plunger 8 with respect to the barrel 5 per rotation with respect to the barrel 5. For example, if the syringe 1 has 100 graduation lines 14 and the plunger 8 advances one graduation line per 180 degree rotation of the plunger 8 with respect to the barrel 5, then the plunger 8 can rotate with respect to the barrel 5 approximately {180 degrees/graduation line 14}*{100 graduation lines 14}=18,000 degrees. The plunger 8 can repeatedly translate with respect to the barrel 5 as they are rotated with respect to each other.

When the plunger 8 is rotated 180 degrees and/or 360 degrees with respect to the barrel 5, the fiducial line 12 can translate greater than approximately 0.1 graduation lines 14, yet more narrowly greater than approximately 0.2 graduation lines 14, yet more narrowly greater than approximately 0.3 graduation lines 14, yet more narrowly greater than approximately 0.4 graduation lines 14, yet more narrowly greater than approximately 0.6 graduation lines 14, yet more narrowly greater than approximately 0.9 graduation lines 14, yet more narrowly greater than approximately 1.4 graduation lines 14, yet more narrowly greater than approximately 1.9 graduation lines 14 or yet more narrowly greater than approximately 3.9 graduation lines 14. When the plunger 8 is rotated 180 degrees and/or 360 degrees with respect to the barrel 5, the fiducial line 12 can translate less than approximately 4.1 graduation lines 14, yet more narrowly less than approximately 2.1 graduation lines 14, yet more narrowly less than approximately 1.6 graduation lines 14, yet more narrowly less than approximately 1.1 graduation lines 14, yet more narrowly less than approximately 0.7 graduation lines 14, yet more narrowly less than approximately 0.6 graduation lines 14, yet more narrowly less than approximately 0.4 graduation lines 14, yet more narrowly less than approximately 0.3 graduation lines 14 or yet more narrowly less than approximately 0.1 graduation lines 14.

The plunger thread pitch 26, the barrel thread pitch 38 and/or the axially oriented distance between two adjacent graduation lines 14 can be larger than about 0.02 in (0.508 mm), yet more narrowly larger than about 0.03 in (0.762 mm), yet more narrowly larger than about 0.04 in (1.016 mm), yet more narrowly larger than about 0.05 in (1.27 mm), yet more narrowly larger than about 0.06 in (1.524 mm), yet more narrowly larger than about 0.07 in (1.778 mm), yet more narrowly larger than about 0.08 in (2.032 mm) yet more narrowly larger than about 0.09 in (2.286 mm) or yet more narrowly larger than about 0.14 in (3.5 mm). The plunger thread pitch 26, the barrel thread pitch 38 and/or the axially oriented distance between two adjacent graduation lines 14 can be smaller than about 0.2 in (5 mm), yet more narrowly smaller than about 0.09 in (2.286 mm), yet more narrowly smaller than about 0.08 in (2.032 mm), yet more narrowly smaller than about 0.07 in (1.778 mm), yet more narrowly smaller than about 0.06 in (1.524 mm), yet more narrowly smaller than about 0.05 in (1.27 mm), yet more narrowly smaller than about 0.04 in (1.016 mm), yet more narrowly smaller than about 0.03 in (0.762 mm) or yet more narrowly smaller than about 0.02 in (0.508 mm). The axially oriented distance between two adjacent graduation lines 14 can be the same and or vary over the length of the barrel 5.

The axially oriented length of the plunger engagement region 51, the barrel engagement region 50 and/or the proximal barrel section 63 can be larger than approximately 0.04 in (1 mm), yet more narrowly larger than approximately 0.08 in (2 mm), yet more narrowly larger than approximately 0.12 in (3 mm), yet more narrowly larger than approximately 0.16 in (4 mm), yet more narrowly larger than approximately 0.2 in (5 mm) or yet more narrowly larger than approximately 0.24 in (6 mm). The axially oriented length of the plunger engagement region 51, the barrel engagement region 50 and/or the proximal barrel section 63 can be less than approximately 0.28 in (7 mm), yet more narrowly less than approximately 0.24 in (6 mm), yet more narrowly less than approximately 0.2 in (5 mm), yet more narrowly less than approximately 0.16 in (4 mm), yet more narrowly less than approximately 0.12 in (3 mm), yet more narrowly less than approximately 0.08 in (2 mm) or yet more narrowly less than approximately 0.04 in (1 mm).

The length of the barrel 5, the barrel sealing region 52, the plunger engagement region 51 and/or the plunger 8 can be larger than 0.5 in (12.7 mm), yet more narrowly larger than about 1.0 in (25.4 mm), yet more narrowly larger than about 1.5 in (38.1 mm), yet more narrowly larger than about 2.0 in (50.8 mm), yet more narrowly larger than about 2.5 in (63.5 mm), yet more narrowly larger than about 3.0 in (76.2 mm), yet more narrowly larger than about 3.5 in (88.9 mm) or yet more narrowly larger than about 4 in (101.6 mm). The length of the barrel 5, the barrel sealing region 52, the plunger engagement region 51 and/or the plunger 8 can be smaller than 6.0 in (101.6 mm), yet more narrowly smaller than about 3.5 in (88.9 mm), yet more narrowly smaller than about 3.0 in (76.2 mm), yet more narrowly smaller than about 2.5 in (63.5 mm), yet more narrowly smaller than about 2.0 in (50.8 mm), yet more narrowly smaller than about 1.5 in (38.1 mm), yet more narrowly smaller than about 1.0 in (25.4 mm) or yet more narrowly smaller than about 0.5 in (12.7 mm).

The plunger 8, the barrel 5, the plunger stopper 6, the barrel thread face 19, the plunger thread face 20, the barrel nut 48 and/or any component of the syringe 1 can have a feature to provide audible or tactile feedback as the plunger 8 is rotated with respect to the barrel 5. For example the barrel tab 41, the barrel dimple 42, the barrel thread face 19, the barrel bump thread 47 and/or the barrel threads 65 can temporarily contact a feature on the plunger 8 when rotated with respect to each other along the longitudinal axis 32. The plunger 8, the barrel 5, the plunger stopper 6, the barrel nut 48, barrel tab 41, the barrel dimple 42, the barrel thread face 19, the barrel bump thread 47 and/or the barrel threads 65 and/or any component of the syringe 1 can move radially outwards and/or inwards when the audible and/or tactile feedback occurs.

The plunger thread pitch 26 and/or the barrel thread pitch 38 can be defined as a fraction and/or multiple of the distance between the graduation lines 14. For example, the plunger thread pitch 26 and/or the barrel thread pitch 38 can be equal to 0.5 times, 1 times and/or 2 times, the distance between two adjacent graduation lines 14. The plunger 8 can advance or retract a predefined distance per rotation, half rotation and/or other angle with respect to the barrel 5. For example, the plunger 8 can advance one half, one and/or two graduation lines 14 per half rotation with respect to the barrel 5. The plunger 8 can advance at a different rate than it retracts when rotating with respect to the barrel 5. For example, when rotating the plunger 8 in the clockwise direction 29 with respect to the barrel 5, the plunger 8 can advance one of the graduation lines 14; when rotating the plunger 8 in the counterclockwise direction with respect to the barrel 5, the plunger 8 can retract two of the graduation lines 14. The plunger 8 can not advance or retract when rotating with respect to the barrel 5. The plunger 8 can advance and/or retract when rotated in the clockwise direction 29 with respect to the barrel 5, but can not advance and/or retract when rotated in the counterclockwise direction with respect to the barrel 5 (or vice-versa). The plunger 8 and/or the barrel 5 can have a feature to prevent the plunger 8 rotating beyond a certain amount with respect to the barrel 5. For example, when the syringe 1 is in the engaged configuration, the plunger 8 and/or the barrel 5 can only transition out of the engaged configuration by rotating the plunger 8 counterclockwise and/or clockwise with respect to the barrel 5. The plunger thread pitch 26 and/or the barrel thread pitch 38 can vary over length of the syringe 1. The distance that the plunger 8 translates when rotating with respect to the barrel 5 can vary over the length of the syringe 1 (e.g., to provide finer and/or coarser resolution at different regions of the syringe 1 and/or graduation lines 14).

The syringe 1 can be used to inject, dispense and/or withdraw various fluids, including medications, medicament, antibiotics, steroids, vaccines, pain killers, lidocaine, insulin, anesthetic, steroids, protein, neurotoxic protein, oral fluids, oral medications, blood, plasma, nutrients, water, saline, adhesive, fibrin, dye, gas, air, pigment and/or oils.

The plunger thread pitch 26 can be different than the barrel thread pitch 38. For example, the plunger thread pitch 26 can be equivalent to 0.25 times, 0.33 times, 0.5 times, 1 times, 2 times, 3 times and/or 4 times the barrel thread pitch 38. The plunger thread pitch angle 33 can be the same and/or different than the barrel thread pitch angle 40.

Along a given cross-section of the syringe 1, the plunger thread face arc angle 37, the sum of the plunger thread face arc angles 37, the barrel thread face arc angle 64, the sum of the barrel thread face arc angles 64, the barrel unthreaded face arc angle 70, the sum of the barrel unthreaded face arc angles 70, the plunger unthreaded face arc angle 71 and/or the sum of the plunger unthreaded face arc angles 71 can be greater than approximately 0 degrees, yet more narrowly larger than approximately 15 degrees, yet more narrowly larger than approximately 30 degrees, yet more narrowly larger than approximately 45 degrees, yet more narrowly larger than approximately 60 degrees, yet more narrowly larger than approximately 90 degrees, yet more narrowly larger than approximately 120 degrees, yet more narrowly larger than approximately 150 degrees, yet more narrowly larger than approximately 180 degrees, yet more narrowly larger than approximately 225 degrees, yet more narrowly larger than approximately 270 degrees, yet more narrowly larger than approximately 315 degrees, yet more narrowly larger than approximately 360 degrees, yet more narrowly larger than approximately 450 degrees, yet more narrowly larger than approximately 540 degrees, yet more narrowly larger than approximately 630 degrees or yet more narrowly larger than approximately 710 degrees. Along a given cross-section of the syringe 1, the plunger thread face arc angle 37, the sum of the plunger thread face arc angles 37, the barrel thread face arc angle 64, the sum of the barrel thread face arc angles 64, the barrel unthreaded face arc angle 70, the sum of the barrel unthreaded face arc angles 70, the plunger unthreaded face arc angle 71 and/or the sum of the plunger unthreaded face arc angles 71 can be less than approximately 720 degrees, yet more narrowly less than approximately 630 degrees, yet more narrowly less than approximately 540 degrees, yet more narrowly less than approximately 450 degrees, yet more narrowly less than approximately 320 degrees, yet more narrowly less than approximately 275 degrees, yet more narrowly less than approximately 230 degrees, yet more narrowly less than approximately 185 degrees, yet more narrowly less than approximately 155 degrees, yet more narrowly less than approximately 125 degrees, yet more narrowly less than approximately 95 degrees, yet more narrowly less than approximately 65 degrees, yet more narrowly less than approximately 50 degrees, yet more narrowly less than approximately 35 degrees, yet more narrowly less than approximately 20 degrees or yet more narrowly less than approximately 5 degrees.

The barrel threads 65 and/or the barrel thread face 19 can be integral to the barrel 5. The barrel threads 65 and/or the barrel thread face 19 can be the same component as the barrel 5. The barrel threads 65 and/or the barrel thread face 19 can be manufactured at the same time as the barrel 5 (e.g., one injection molded) and/or can be formed after the initial manufacturing of the barrel 5 (e.g., the barrel threads 65 and/or the barrel thread face 19 can be formed or cut from the barrel 5). The barrel threads 65 and/or the barrel thread face 19 can be a separate component than the barrel 5. The barrel threads 65 and/or the barrel thread face 19 can be rotationally and/or longitudinally fixed to the barrel 5. The barrel threads 65 and/or the barrel thread face 19 can be a wire form that is rotationally and/or longitudinally fixed to the barrel 5.

The plunger threads 66 and/or the plunger thread face 20 can be integral to the plunger 8. The plunger threads 66 and/or the plunger thread face 20 can be the same component as the plunger 8. The plunger threads 66 and/or the plunger thread face 20 can be manufactured at the same time as the plunger 8 (e.g., one injection molded) and/or can be formed after the initial manufacturing of the plunger 8 (e.g., the plunger threads 66 and/or the plunger thread face 20 can be formed or cut from the plunger 8). The plunger threads 66 and/or the plunger thread face 20 can be a separate component than the plunger 8. The plunger threads 66 and/or the plunger thread face 20 can be rotationally and/or longitudinally fixed to the plunger 8. The plunger threads 66 and/or the plunger thread face 20 can be a wire form that is rotationally and/or longitudinally fixed with respect to the plunger 8.

The frictional force, radial force, glide force, axial glide force, the radial glide force, the break-loose force, the axial break-loose force and/or the rotational break-loose force between the barrel 5, the plunger 8 and/or the plunger stopper 6 can be greater than approximately 0.5 N, yet more narrowly larger than approximately 1 N, yet more narrowly larger than approximately 2.5 N, yet more narrowly larger than approximately 4.5 N, yet more narrowly larger than approximately 7.5 N, yet more narrowly larger than approximately 9.5 N or yet more narrowly larger than approximately 15 N. The frictional force, radial force, glide force, axial glide force, the radial glide force, the break-loose force, the axial break-loose force and/or the rotational break-loose force between the barrel 5, the plunger 8 and/or the plunger stopper 6 can be less than approximately 20 N, yet more narrowly less than approximately 16 N, yet more narrowly less than approximately 10 N, yet more narrowly less than approximately 8 N, yet more narrowly less than approximately 5 N, yet more narrowly less than approximately 3 N, yet more narrowly less than approximately 2 N or yet more narrowly less than approximately 1 N. The syringe 1 can function better if the torque, frictional force between the barrel 5, the plunger 8 and/or the plunger stopper 6 is high enough to prevent accidental displacement of the plunger 8 with respect to the barrel 5. The torque, frictional force and/or radial force to rotate the plunger 8 with respect to the barrel 5 may vary by angle. For example, the force to rotate the plunger 8 with respect to the barrel 5 may be very low when the syringe 1 is in the disengaged configuration and may increase to a peak when the syringe 1 is in the middle of the engaged configuration. The force to rotate the plunger 8 with respect to the barrel 5 may be higher when the syringe 1 is in the engaged configuration than when the syringe 1 is in the disengaged configuration. The force to rotate the plunger 8 may be higher when transitioning between the engaged and/or the disengaged configurations. For example, the plunger 8 may be biased to remain in the disengaged and/or the engaged configuration. For example, the higher torque, radial force and/or frictional force may occur when the plunger 8 is approximately halfway between the engaged and the disengaged configuration. For example, if the syringe 1 is in the disengaged configuration when the plunger 8 is at 0 degrees or 180 degrees with respect to the barrel 5 and in the engaged configuration when the plunger 8 is at 90 degrees or 270 degrees with respect to the barrel 5, then the highest torque, radial force and/or frictional force may occur when the plunger 8 is at approximately 45, 135, 225 and/or 315 degrees with respect to the barrel 5; in other words the engaged and/or the disengaged configurations may be at lower energy states than when transitioning between the engaged and/or the disengaged configuration. As the plunger 8 is rotated with respect to the barrel 5, the plunger 8 may be biased to remain in certain angular positions (e.g., due to the camming effect of the ovalization of the barrel 5, the plunger thread 66 and/or the barrel thread 65; due to the barrel dimple 42; due to the barrel flat 43; and/or due to the barrel squeeze points 44).

The torque to rotate the plunger 8 with respect to the barrel 5 may be greater than approximately 0.05 Ncm, yet more narrowly greater than approximately 0.1 Ncm, yet more narrowly greater than approximately 0.3 Ncm, yet more narrowly greater than approximately 0.5 Ncm, yet more narrowly greater than approximately 1 Ncm, yet more narrowly greater than approximately 2 Ncm and/or yet more narrowly greater than approximately 5 Ncm. The torque to rotate the plunger 8 with respect to the barrel 5 may be less than approximately 5 Ncm, yet more narrowly less than approximately 3 Ncm, yet more narrowly less than approximately 2 Ncm, yet more narrowly less than approximately 1 Ncm, yet more narrowly less than approximately 0.5 Ncm, yet more narrowly less than approximately 0.3 Ncm and/or yet more narrowly less than approximately 0.1 Ncm.

The inner circumference of the barrel 5 can be the shortest path that contacts all radially internal points (e.g., all points on the inner wall) along a cross-section of the barrel 5. The inner circumference of the barrel 5 can be the shortest circular and/or oval path that excludes all points along a cross-section of the barrel 5.

The external circumference of the plunger 8 can be the shortest path that contacts all radially external points (e.g., all points on the external wall) along a cross-section of the plunger 8. The external circumference of the plunger 8 can be the shortest circular and/or oval path that encloses all radially external points (e.g., all points on the external wall) along a cross-section of the plunger 8.

The pitch of the barrel thread 65 and/or the plunger thread 66 can be different than the lead. For example, the barrel thread 65 and/or the plunger thread 66 can have multiple starts; in which case, the lead can be equal to the pitch multiplied by the number of starts. The position of the barrel thread 65, the plunger thread 66 can be designed such that the fiducial line 12 is approximately aligned with the graduation line 14 when the plunger 1 is in the engaged and/or disengaged configuration. For example, each half and/or complete rotation of the plunger 8 with respect to the barrel 5 can end with the fiducial line 12 on the graduation line 14. For example, if the operator translated and/or depresses the plunger 8 to a position half-way between two graduation lines 14 and then rotates the plunger 8 with respect to the barrel 5 in the clockwise direction 29 from the disengaged, to the engaged and to the disengaged configuration, the plunger 8 can advance and/or retract 0.5 and/or 1.5 graduation lines 14 such that the fiducial line 12 is on the graduation line 14. The torque to rotate the plunger 8 with respect to the barrel 5 can be different at various rotational and/or longitudinal positions. For example, the torque can increase every other transition from the disengaged to the engaged configuration. The plunger thread face 20*a* and/or 20*b* can alternately engage with the barrel thread face 19*a* and/or 19*b*. The torque required to rotate the plunger 8 with respect to the barrel 5 can be low and then temporarily increase to indicate when the syringe 1 is transitioning between the engaged and disengaged configurations. The plunger thread face 20 can refer to the sum of all of the plunger thread faces 20. The barrel thread face 20 can refer to the sum of all of the barrel thread faces 20. The plunger unthreaded face 21 can refer to the sum of all of the plunger unthreaded faces 21. The barrel unthreaded face 49 can refer to the sum of all of the barrel unthreaded faces 49. The plunger thread arc length 35 can refer to the sum of all of the plunger thread arc lengths 35. The barrel thread arc length 69 can refer to the sum of all of the barrel thread arc lengths 69. The plunger thread face arc length 77 can refer to the sum of all of the plunger thread face arc lengths 77. The barrel thread face arc length 78 can refer to the sum of all of the barrel thread face arc lengths 78. The plunger thread face arc angle 37 can refer to the sum of all of the plunger thread face arc angles 37. The barrel thread face arc angle 64 can refer to the sum of all of the barrel thread face arc angles 64. The barrel unthreaded face arc angle 70 can refer to the sum of all of the barrel unthreaded face arc angles 70. The plunger unthreaded face arc angle 71 can refer to the sum of all of the plunger unthreaded face arc angles 71. The The torque to rotate the plunger 8 with respect to the barrel 5 can be larger than approximately 0.1 Nm, yet more narrowly larger than approximately 0.5 Nm, yet more narrowly larger than approximately 1 Nm, yet more narrowly larger than approximately 2 Nm, yet more narrowly larger than approximately 4 Nm, yet more narrowly larger than approximately 6 Nm, yet more narrowly larger than approximately 8 Nm or yet more narrowly larger than approximately 10. The torque to rotate the plunger 8 with respect to the barrel 5 can be less than approximately 10 Nm, yet more narrowly less than approximately 8 Nm, yet more narrowly less than approximately 6 Nm, yet more narrowly less than approximately 4 Nm, yet more narrowly less than approximately 2 Nm, yet more narrowly less than approximately 0.5 Nm or yet more narrowly less than approximately 0.1 Nm.

The syringe 1 can withdraw and/or dispense a fluid. The syringe 1 can have the barrel 5 having the barrel thread face 19 across the barrel thread face arc angle 64 at a first cross-section, wherein the barrel thread face 19 can have the helical internal barrel thread 65. The syringe 1 can have the plunger 8 having the plunger body, wherein at least a length of the plunger 8 can be in the barrel 5, wherein the plunger 8 can have the plunger thread face 20 across the plunger thread face arc angle 37 at the first cross-section, wherein the plunger thread face 20 can have first, second and third helical external plunger threads 66*a*, 66*b* and 66*c* integral with the plunger body and/or the plunger 8. The barrel thread face arc angle 64 added to the plunger thread face arc angle 37 at the first cross-section can be less than 360 degrees. The sum of all of the barrel thread face arc angles 64 added to the plunger thread face arc angles 37 at the first cross-section can be less than 360 degrees. The barrel unthreaded face arc angle 70 added to the plunger unthreaded face arc angle 71 at the first cross-section can be greater than 360 degrees. The sum of all of the barrel unthreaded face arc angles 70 added to the plunger unthreaded face arc angles 71 at the first cross-section can be greater than 360 degrees. The sum of the plunger thread face arc angles 37 and the plunger unthreaded face arc angles 71 at the first cross-section can be 360 degrees. The sum of the barrel thread face arc angles 64 and the barrel unthreaded face arc angles 71 at the first cross-section can be 360 degrees. The sum of the plunger thread face arc angles 37, the plunger unthreaded face arc angles 71, the barrel thread face arc angles 64 and the barrel unthreaded face arc angles 71 at the first cross-section can be 720 degrees. In a first configuration, the plunger 8 can be rotated 0 degrees with respect to the barrel 5 and the barrel 5 can be at a first longitudinal position with respect to the plunger 8. In a second configuration, the plunger 8 can be rotated 360 degrees with respect to the barrel 5 and the barrel 5 can be at a second longitudinal position with respect to the plunger 8. In the first configuration, the helical internal barrel thread 65 can be engaged with the first and second helical external plunger threads 66*a* and/or 66*b*. In the second configuration, the helical internal barrel thread 65 can be engaged with the third helical external plunger thread 66*c*. The barrel thread 65 can be helical and internal. The plunger thread 66 can be helical and external.

The helical internal barrel thread 65 can have the barrel thread pitch angle 40 with respect to the longitudinal axis 32. A barrel thread helix angle can be the barrel thread pitch angle 40. The barrel thread helix angle and/or the thread helix angle can be less than 90 degrees, yet more narrowly less than 80 degrees or yet more narrowly less than 60 degrees. The barrel thread helix angle and/or the thread helix angle can be greater than 60 degrees, yet more narrowly greater than 70 degrees or yet more narrowly greater than 80 degrees. A thread helix angle can be the barrel thread pitch angle 40. The plunger thread pitch angle 33 can be the plunger thread helix angle and/or the thread helix angle.

The syringe 1 can or can not have any rotational stops for impeding a rotation of the plunger 8 with respect to the barrel 5 when the plunger 8 is located within the barrel 5 and/or the plunger thread face 19 is at the same cross-section as the barrel thread face 20.

The plunger 8 can be rotated 450 degrees with respect to the barrel 5 when the plunger 8 is located within the barrel 5 and/or the plunger thread face 19 is at the same cross-section as the barrel thread face 20. The syringe 1 can be in a third configuration when the plunger 8 is rotated 450 degrees with respect to the barrel 5 when the plunger 8 is located within the barrel 5 and/or the plunger thread face 19 is at the same cross-section as the barrel thread face 20.

The syringe 1 can have the barrel 5 having a barrel body. The barrel thread 65 and/or the barrel thread face 19 can be rotationally and/or longitudinally fixed with respect to the barrel body. The barrel thread 65 and/or the barrel thread face 19 can be rotationally and/or longitudinally fixed with respect to the barrel 5.

The barrel 5 can have more than one barrel thread face 19 across more than one barrel thread face arc angle 64 at the first cross-section. The plunger 8 can have more than one plunger thread face 20 across more than one plunger thread face arc angle 37 at the first cross-section. The sum of the barrel thread face arc angles 64 added to the sum of the plunger thread face arc angles 37 at the first cross-section can be less than 360 degrees.

The syringe 1 can have a barrel 5 with the barrel inner circumference. The barrel 5 can have the barrel inner surface 68. The barrel inner surface 68 can comprise all points on the radially interior wall of the barrel 5. The barrel inner surface 68 can have the barrel first thread face 19*a*. The barrel first thread face 19*a* can have the barrel first thread 65*a*. The barrel first thread 65*a* can have the barrel first thread arc length 69*a*, the barrel first thread face arc length 78*a*, the barrel first thread arc angle 79*a* and/or the barrel first thread face arc angle 64*a*. The barrel first thread face 19*a* can have the barrel first thread arc length 69*a*, the barrel first thread face arc length 78*a*, the barrel first thread arc angle 79*a* and/or the barrel first thread face arc angle 64*a*. The barrel first thread arc length 69*a* and/or the barrel first thread face arc length 78*a* can be less than the inner circumference of the barrel 5. The barrel first thread 65*a* can be helical. The syringe 1 can have the plunger 8. The plunger 8 can have the plunger outer circumference. At least a length of the plunger 8 can be in the barrel 5. The plunger 8 can have the plunger first thread face 20*a* on a length of the plunger 8. The plunger first thread face 20*a* can have the plunger first thread 66*a*. The plunger first thread arc length 35 and/or the plunger first thread face arc length 77*a* can be less than the outer circumference of the plunger 8. The plunger first thread 66*a* can be helical. The plunger first thread face 20*a* can have the plunger first thread arc length 35*a*, the plunger first thread face arc length 77*a*, the plunger first thread arc angle 80*a* and/or the plunger first thread face arc angle 37*a*. The plunger first thread 66*a* can have the plunger first thread arc length 35*a*, the plunger first thread face arc length 77*a*, the plunger first thread arc angle 80*a* and/or the plunger first thread face arc angle 37*a*. The plunger first thread arc length 35*a* can be less than the outer circumference of the plunger 8. The first plunger thread 65*a* can be helical. The plunger first thread arc angle 80*a* added to the barrel first thread arc angle 79*a* can be less than 360 degrees. The sum of multiple plunger thread arc angles 80 added to the sum of multiple barrel thread arc angles 79 can be less than 360 degrees, yet more narrowly less than 315 degrees, yet more narrowly less than 270 degrees, yet more narrowly less than 225 degrees, yet more narrowly less than 180 degrees, yet more narrowly less than 135 degrees, yet more narrowly less than 90 degrees and/or yet more narrowly less than 45 degrees. The sum of multiple plunger thread arc angles 80 added to the sum of multiple barrel thread arc angles 79 can be greater than 45 degrees, yet more narrowly greater than 90 degrees, yet more narrowly greater than 135 degrees, yet more narrowly greater than 180 degrees, yet more narrowly greater than 225 degrees, yet more narrowly greater than 270 degrees, yet more narrowly greater than 315 degrees and/or yet more narrowly greater than 360 degrees. The sum of multiple plunger thread face arc angle 37 added to the sum of multiple barrel thread face arc angle 64 can be less than 360 degrees, yet more narrowly less than 315 degrees, yet more narrowly less than 270 degrees, yet more narrowly less than 225 degrees, yet more narrowly less than 180 degrees, yet more narrowly less than 135 degrees, yet more narrowly less than 90 degrees and/or yet more narrowly less than 45 degrees. The sum of multiple plunger thread face arc angle 37 added to the sum of multiple barrel thread face arc angle 64 can be greater than 45 degrees, yet more narrowly greater than 90 degrees, yet more narrowly greater than 135 degrees, yet more narrowly greater than 180 degrees, yet more narrowly greater than 225 degrees, yet more narrowly greater than 270 degrees, yet more narrowly greater than 315 degrees and/or yet more narrowly greater than 360 degrees.

The syringe 1 can comprise the plunger stopper 6 attached to the plunger 8. The plunger stopper 6 can form a fluid tight seal with the barrel inner surface 68. The plunger stopper 6 can form a fluid tight seal with the barrel 5. The plunger 8 can form a fluid-tight seal with the barrel inner surface 68. The plunger 8 can form a fluid-tight seal with the barrel 5.

The barrel inner surface 68 can have the barrel first unthreaded face 49*a*. The barrel first unthreaded face 49*a* can be angularly offset from the barrel first thread face 19*a*. The barrel first unthreaded face arc angle 70*a* can be greater than 10 degrees, yet more narrowly greater than 25 degrees or yet more narrowly greater than 45 degrees. The barrel first unthreaded face arc angle 70*a* can be less than 60 degrees, yet more narrowly less than 30 degrees or yet more narrowly less than 15 degrees.

The barrel inner surface 68 can have the barrel second thread face 19*b*. The barrel second thread face can be angularly offset from the barrel first thread face 19*a*. The barrel inner surface 68 can have the barrel first unthreaded face 49*a* angularly between the barrel first thread face 19*a* and the barrel second thread face 19*b*.

The barrel inner surface 68 can have the second barrel unthreaded face 49*b*. The second barrel unthreaded face 49*b* can be angularly between the barrel first thread face 19*a* and the barrel second thread face 19*b*. The second barrel unthreaded face 49*b* can be on the angularly opposite side of the barrel first thread face 19*a* as the barrel first unthreaded face 49*a*.

The barrel unthreaded face arc angle 70 and/or the arc angle of the barrel first unthreaded face 49*a* can be at least 5 degrees, yet more narrowly greater than 25 degrees or yet more narrowly greater than 45 degrees. The barrel unthreaded face arc angle 70 and/or the arc angle of the barrel first unthreaded face 49*a* can be less than 60 degrees, yet more narrowly less than 45 degrees, yet more narrowly less than 30 degrees.

The plunger 8 can be rotatable with respect to the barrel 5. The plunger 8 can be rotatable with respect to the barrel 5 when the plunger 8 is in the barrel 5. The plunger 8 can be rotatable with respect to the barrel 5 when the syringe 1 is in the engaged and/or disengaged configuration.

In a first configuration, the barrel 5 can be rotated 0 degrees with respect to the plunger 8 and the barrel 5 can be at a first longitudinal position with respect to the plunger 8. In a second configuration, the barrel 5 can be rotated 180 degrees with respect to the plunger 8 and the barrel 5 can be at a second longitudinal position with respect to the plunger 8 that can be different than the first longitudinal position.

The barrel first thread 65*a* can helically and/or threadedly interface with the plunger first thread 66*a*.

The syringe 1 can be used to dispense a fluid. The syringe 1 can comprise the plunger 8 having the plunger thread 66 and the barrel 5 having the barrel thread 65. The plunger 8 can be rotated with respect to the barrel 5 when the plunger 8 starts at a first longitudinal position with respect to the barrel 5; wherein rotating can comprise engaging the plunger thread 66 with the barrel thread 65 and longitudinally moving the plunger 8 with respect to the barrel 5 from the first longitudinal position. Rotating can comprise rotating the plunger 8 an angle with respect to the barrel 5, while the plunger 8 is concentric and/or coaxial with the barrel 5. The plunger 8 can be depressed with respect to the barrel 5 when the plunger 8 can start at the first longitudinal position with respect to the barrel 5; wherein depressing of the plunger 8 can comprise moving the plunger 8 only in the direction of the longitudinal axis 32 of the plunger 8. The plunger 8 can and/or can not rotate with respect to the barrel 5 when the plunger 8 is depressed. A first radial distance from the plunger thread 66 to the longitudinal axis 32 of the plunger 8 when rotating the plunger 8 can be equal to a second radial distance from the plunger thread 66 to the longitudinal axis 32 of the plunger 8 when depressing the plunger 8. A third radial distance from the barrel thread 65 to the longitudinal axis 32 of the plunger 8 when rotating the plunger 8 can be equal to a fourth radial distance from the barrel thread 65 to the longitudinal axis 32 of the plunger 8 when depressing the plunger 8. The radial distance from the plunger thread 66 and/or the barrel thread 65 to the longitudinal axis 32 can be constant when rotating, depressing and/or translating the plunger 8 with respect to the barrel 5. The radial distance from the plunger thread 66 to the longitudinal axis 32 can be constant and/or fixed. The radial distance from the barrel thread 65 to the longitudinal axis 32 can be constant and/or fixed. The radial distance from the plunger thread 66 to the longitudinal axis 32 can change. The radial distance from the barrel thread 65 to the longitudinal axis 32 can change.

Depression and/or translation of the plunger 8 with respect to the barrel 5 can be locked out when the syringe 1 is in the engaged and/or locked configuration. The syringe 1 can transition between the engaged and disengaged configurations by rotating the plunger 8 90 degrees with respect to the barrel 5. If the syringe 1 is the disengaged and/or unlocked configuration, rotating the plunger 8 by more than 90 degrees with respect to the barrel 5 can cause the syringe 1 to be in the engaged and/or locked configuration. If the syringe 1 is the engaged and/or locked configuration, rotating the plunger 8 by more than 90 degrees in the same direction with respect to the barrel 5 can cause the syringe 1 to be in the disengaged and/or unlocked configuration. Rotating the plunger 8 with respect to the barrel 5 can repeatedly and sequentially lockout depression of the plunger 8 with respect to the barrel 5 and unlock depression of the plunger 8 with respect to the barrel 5. Rotating the plunger 8 with respect to the barrel 5 can repeatedly and sequentially cause the syringe 1 be in the engaged configuration and the disengaged configuration.

Figure 23:
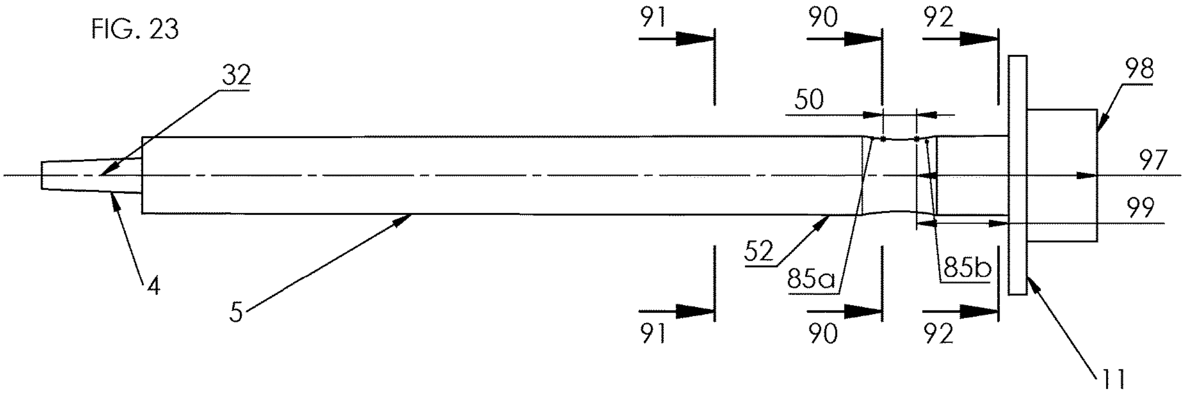
FIG. 23 is a side view of the barrel.

FIG. 23 illustrates that the barrel engagement 50 region may be at any point along the barrel 5. FIG. 23 illustrates the location of a first cross sectional slice 90 of the barrel 5 that is further illustrated in FIG. 24*b*. The first cross sectional slice 90 may pass through barrel engagement region 50. FIG. 23 illustrates the location of a second cross sectional slice 91 of the barrel 5 that is further illustrated in FIG. 24*a*. FIG. 23 illustrates the location of a third cross sectional slice 92 of the barrel 5 that is further illustrated in FIG. 24*c*. FIG. 23 illustrates that the transition from the barrel sealing region 52 to the barrel engagement region 50 may be gradual and/or flared. The first cross sectional slice 90, the second cross sectional slice 91 and/or the third cross sectional slice 92 may be perpendicular to the longitudinal axis 32. The second cross sectional slice 91 may be in the barrel sealing region 52 and/or may be distal to the first cross sectional slice 90. The third cross sectional slice 91 may be in the barrel sealing region 52 and/or may be proximal to the first cross sectional slice 90.

Figure 24A:
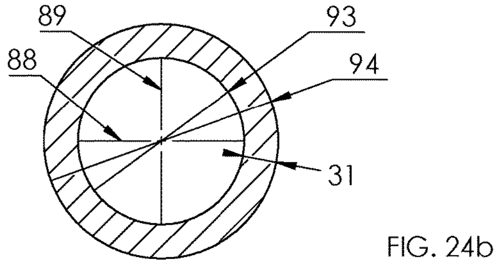
FIG. 24*a* is a cross sectional slice view at a first cross sectional slice 91.
Figure 24C:
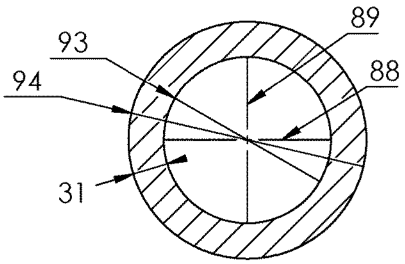
FIG. 24*c* is a cross sectional slice view at a third cross sectional slice 92.
Figure 24B:
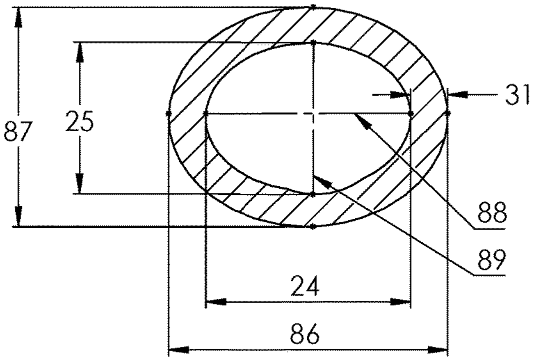
FIG. 24*b* is a cross sectional slice view at a second cross sectional slice 90.

FIG. 24*a* illustrates a barrel inner diameter 93 and a barrel outer diameter 94 at the second cross-sectional slice 91 of the barrel 5. The cross-section of the barrel 5 at the second cross-sectional slice 91 of the barrel 5 may be circular, rectangular, triangular, oblong, oval and/or approximately circular. FIG. 24*b* illustrates the barrel nut width 24 and the barrel nut height 25 at the first cross-sectional slice 90 of the barrel 5. The cross-section of the barrel 5 at the first cross-sectional slice 90 of the barrel 5 may be circular, triangular, rectangular, oblong, oval and/or approximately circular. FIG. 24*c* illustrates the barrel inner diameter 93 and the barrel outer diameter 94 at the third cross-sectional slice 92 of the barrel 5. The cross-section of the barrel 5 at the second cross-sectional slice 92 of the barrel 5 may be circular, triangular, rectangular, oblong, oval and/or approximately circular. The barrel inner diameter 93, the barrel nut height 25 and/or the barrel nut width 24 may be the same dimension and/or different at all points along the barrel 5. For example, the barrel inner diameter 93 at the second cross sectional slice 91 may be the same and/or different than the barrel inner diameter 93 at the third cross sectional slice 92. The barrel outer diameter 94 may be the same dimension and/or different at all points along the barrel 5. For example, the barrel outer diameter 94 at the second cross sectional slice 91 may be the same and/or different than the barrel outer diameter 94 at the third cross sectional slice 92. The barrel wall thickness 31 may be the same dimension and/or different at all points along the barrel 5. For example, the barrel wall thickness 31 may be the same and/or different at the first cross-sectional slice 90, the second cross-sectional slice 91 and/or the third cross-sectional slice 92. A barrel engagement transition region 85*a* and/or 85*b* may gradually transition between the first cross-sectional slice 90, the barrel engagement region 50, the barrel sealing region 52, the second cross sectional slice 91 and/or the third cross sectional slice 92. The barrel engagement transition region 85*a* and/or 85*b* may transition abruptly from the first cross-sectional slice 90, the barrel engagement region 50, the barrel sealing region 52, the second cross sectional slice 91 and/or the third cross sectional slice 92. The barrel engagement transition region 85*a* and/or 85*b* may approximate a lofted feature from the first cross-sectional slice 90, the barrel engagement region 50, the barrel sealing region 52, the second cross sectional slice 91 and/or the third cross sectional slice 92. A barrel nut outside width 86 may be equal to the barrel nut width 24 added to twice the barrel wall thickness 31. A barrel nut outside height 87 may be equal to the barrel nut height 25 added to twice the barrel wall thickness 31. The barrel nut width 24, the barrel nut height 25, the barrel nut outside width 86, the barrel nut outside height 87 and/or the barrel wall thickness 31 may vary as the plunger 8 rotates with respect to the barrel 5. For example, the barrel nut outside height 87 may be larger and/or smaller when the syringe 1 is in the engaged configuration than when it is in the disengaged configuration. For example, the barrel nut outside width 87 may be smaller and/or larger when the syringe 1 is in the engaged configuration than when it is in the disengaged configuration. The barrel 5 and/or the plunger 8 may have a barrel major axis 88 and/or a barrel minor axis 89. The barrel major axis 88 may be equal to, larger and/or smaller than the barrel minor axis 89. For example, the cross-section of the barrel 5 at the second cross-sectional slice 91 and/or the third cross-sectional slice 92 of the barrel 5 may be circular, in which case the barrel major axis 88 may be equal to the barrel minor axis 89. A minimum internal radius and/or a maximum internal radius of a cross-section of the barrel 5 may be equal. A maximum external radius and/or a minimum external radius of a cross-section of the barrel 5 may be equal. The cross-section of the barrel 5 may be symmetric about the barrel major axis 88 and/or the barrel minor axis 89.

Figure 25:
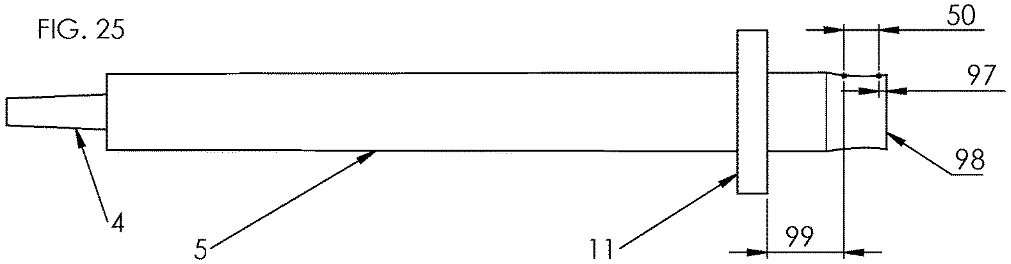
FIG. 25 is a side view of the barrel.

FIG. 25 illustrates that the barrel engagement region 50 may be at and/or near a barrel proximal end 98 of the barrel 5. The barrel flange 11 may be proximal and/or distal to the barrel engagement region 50. Having the barrel engagement region 50 at and/or near the barrel proximal end 98 may reduce contact between the plunger thread face 20 and the barrel 5 when the syringe 1 is in the disengaged configuration. For example, if the plunger 8 is translated with respect to the barrel 5, then the plunger thread 66 may inadvertently and/or purposely contact a portion of the barrel 5, such as the barrel proximal end 98 and/or the barrel ramp 22. If the plunger thread 66 contacts the barrel 5 when the plunger 8 is being translated in the disengaged configuration, then there may be additional resistance and/or tactile feedback. Having the barrel engagement region 50 at and/or near the barrel proximal end 98 may provide smoother translation of the plunger 8 when in the disengaged configuration.

Figure 26A:
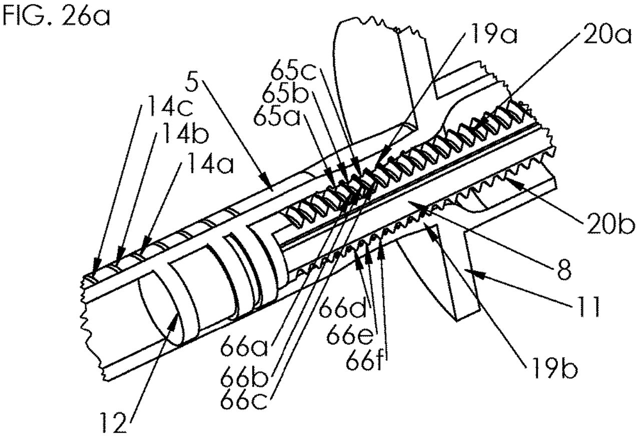
FIG. 26*a* through FIG. 26*e* are illustrative isometric views of a proximal section of the syringe with a left half of the barrel removed.
Figure 26B:
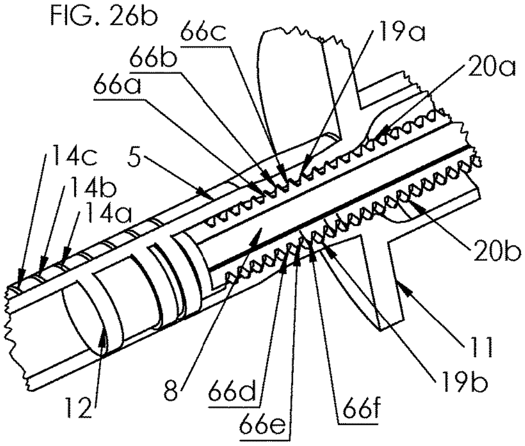
Figure 26C:
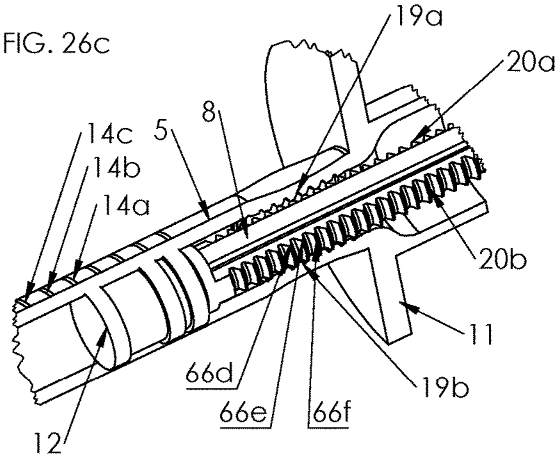
Figure 26D:
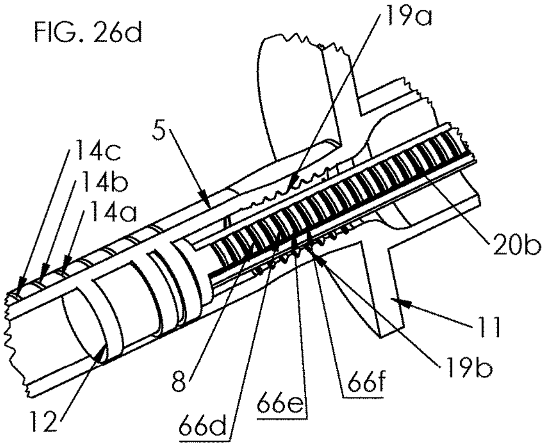
Figure 26E:
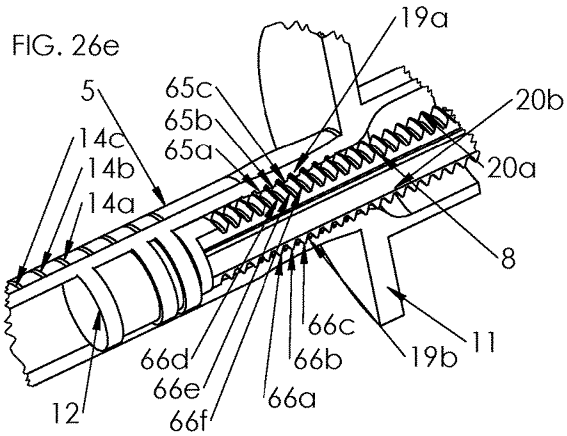

FIG. 26*a* illustrates the syringe 1 in the engaged configuration, with the fiducial line 12 at approximately the graduation line 14*a*. In the engaged configuration, the plunger thread faces 20*a* and/or 20*b* can be engaged and/or locked with the barrel thread faces 19*a* and/or 19*b*. In the engaged configuration, the volume of fluid contained within syringe 1 can not be adjusted significantly. FIG. 26*b* illustrates the plunger 8 rotated 45 degrees in the clockwise direction 29 with respect to the plunger 8 position illustrated in FIG. 26*a*. Depending on the barrel thread face arc angle 64 and the plunger thread face arc angle 37, the syringe 1 can be in the engaged and/or disengaged configuration. When the plunger 8 is rotated with respect to the barrel 5 in the engaged configuration, the plunger 8 can remain longitudinally fixed with respect to the barrel 5. For example, the plunger thread 66 and/or the barrel thread 65 can be perpendicular to the longitudinal axis 32. FIG. 26*c* illustrates the plunger 8 rotated 45 degrees in the clockwise direction 29 with respect to the plunger 8 position illustrated in FIG. 26*b*. FIG. 26*c* illustrates that the syringe 1 can be in the disengaged configuration when the plunger thread face 20 is not in contact with the barrel thread face 19. In the disengaged configuration, the plunger 8 can be translated longitudinally with respect to the barrel 5 with and/or without rotating the plunger 8 with respect to the barrel 5. FIG. 26*d* through FIG. 26*e* illustrate the plunger 8 rotating with respect to the barrel 5 an additional 45 degrees per figure. FIG. 26*e* illustrates the plunger 8 rotating 180 degrees with respect to the orientation of the plunger 8 illustrated in FIG. 26*a*. FIG. 26*a* through FIG. 26*e* illustrate that rotating the plunger 8 with respect to the barrel 5 can maintain the plunger 8 longitudinally fixed with respect to the barrel 5. For example, compared to the starting position in FIG. 26*a*, FIG. 26*e* illustrates that the plunger 8 and/or the fiducial line 12 can remain at approximately the same graduation line 14*a*. The plunger 8 can continue to rotate with respect to the barrel 5 by repeating the same steps illustrated in FIG. 26*a* through FIG. 26*e*. The plunger 8 can be rotated in the counterclockwise direction (e.g., a direction opposite the clockwise direction 29) relative to the barrel 5, as illustrated in the reverse sequence of FIG. 26 (e.g., FIG. 26*e* through FIG. 26*a*). If the plunger 8 is rotated in the counterclockwise direction relative to the barrel 5, the plunger 8 may remain approximately longitudinally fixed with the fiducial line at graduation line 14*a*.

Figure 27:
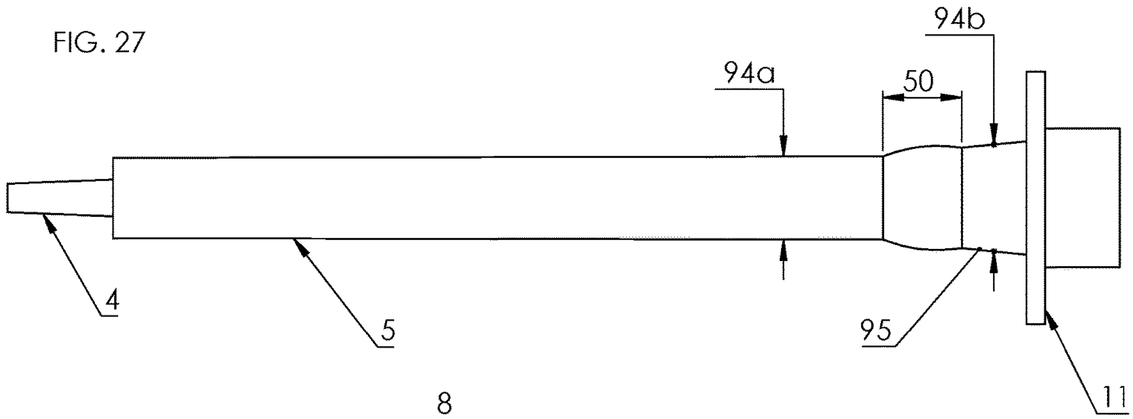
FIG. 27 is a side view of the barrel.

FIG. 27 illustrates that the barrel inner diameter 93 and/or the barrel outer diameter 94 may be larger proximal to the barrel engagement region 50. For example the barrel outer diameter 94*b* may be larger than the barrel outer diameter 94*a*. A barrel flared region 95 may reduce contact of the plunger thread 66 with points of the barrel 5 that are not in the barrel engagement region 50.

Figure 28:
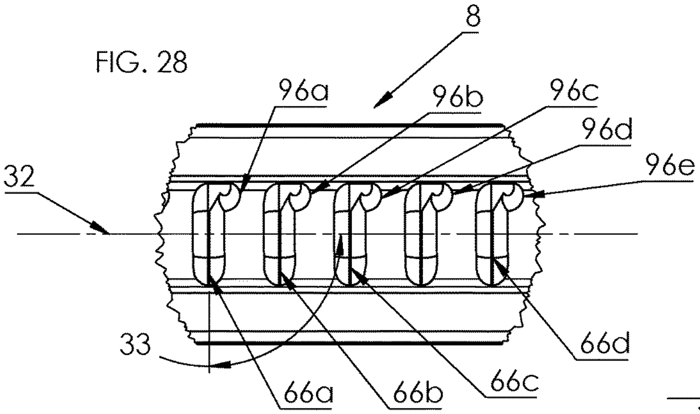
FIG. 28 is a side view of a short section of the plunger.

FIG. 28 illustrates that the plunger threads 66 may have various profiles. For example, the plunger thread 66 may include a thread bump 96. The thread bump 96 may ensure that the plunger 8 translates distally when the syringe 1 transitions from the disengaged configuration to the engaged configuration and/or vice-versa. For example, it may be beneficial to bias the plunger 8 distally when transitioning between the engaged and/or disengaged configurations. For example, it may be disadvantageous to draw air into the syringe 1 (e.g., air can cause an embolic event and/or reduce the accuracy of a medication being administered). For example, to avoid drawing air into the syringe 1 it may be beneficial to always bias the plunger 8 distally when locking and/or unlocking the syringe 1 (e.g., when transitioning between the engaged and/or disengaged configurations). The thread bump 96 may be on the plunger 8 and/or the barrel 5. The plunger thread pitch angle 33 may be approximately 90 degrees.

Figure 29:
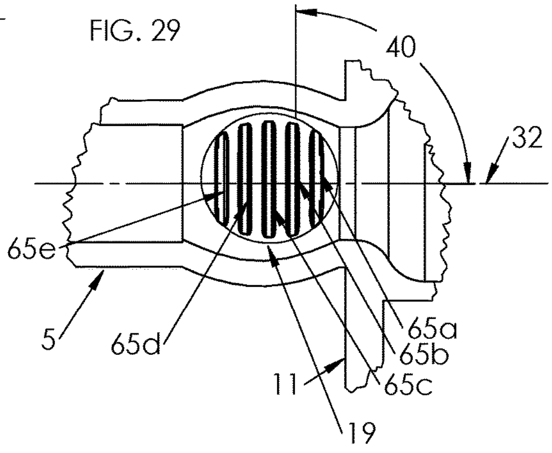
FIG. 29 is a top view of the barrel engagement region of the barrel with the top half of the barrel removed.

FIG. 29 illustrates that the barrel thread face 19 may be circular and/or oval. The barrel thread pitch angle 40 may be approximately 90 degrees.

Figure 30:
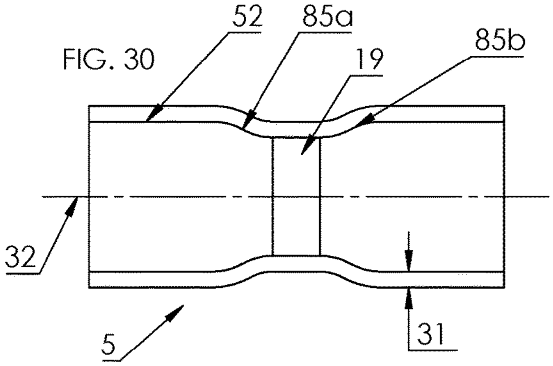
FIG. 30 is a top view of the barrel engagement region of the barrel with the top half of the barrel removed. The barrel threads are not shown in the illustration.

FIG. 30 illustrates that the barrel engagement transition region 85 may be from the barrel thread face 19 to the barrel sealing region 52 and/or other sections of the barrel 5 may be smooth. The barrel engagement transition region 85 may be lofted, splined, a 1st order spline, a multiple order spline, smooth, abrupt, curved, filleted, linear and/or chamfered.

Figure 31:
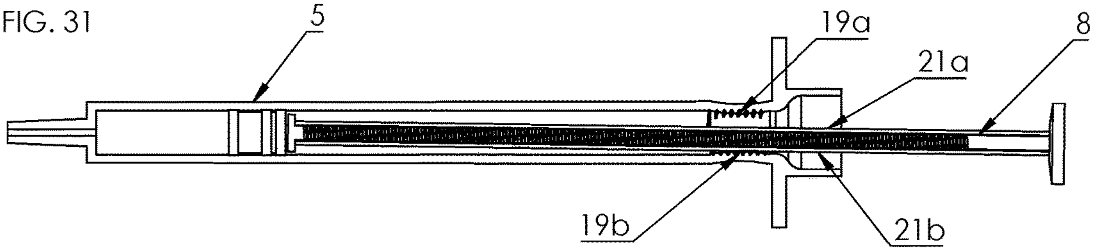
FIG. 31 is an illustrative side view of the barrel with the left half of the barrel removed.

FIG. 31 illustrates that the plunger 8 may be angled with respect to the barrel 5. For example, the plunger 8 may be angled and/or bent if a load is applied perpendicular to the longitudinal axis 32. For example, the plunger 8 may be bent or buckle if it is pressed distally. The plunger unthreaded face 21 may contact the barrel thread face 19. For example, FIG. 31 illustrates that the plunger unthreaded face 21*b* may contact the barrel threaded face 19*b*. The plunger unthreaded face 21 may be configured to provide smooth longitudinal travel when contacting the barrel thread face 19. For example, the plunger unthreaded face 21 may contain sharp and/or smooth edges, rails, grooves and/or different durometers.

The syringe 1 may be in the disengaged configuration and/or the engaged configuration for all volumes of the syringe 1. For example, the syringe 1 may be in the engaged and/or disengaged configuration at any volume of the syringe from approximately 0 up to approximately the nominal capacity 13. The syringe 1 may be in the engaged and/or disengaged configuration at any point of the barrel 5. For example, the syringe 1 may be in the engaged configuration at any of the graduation line 14 and/or in-between the graduation lines 14. The syringe 1 may be in the engaged configuration every 1/10 of the spacing between two adjacent graduation lines 14, yet more narrowly every 1/8 of the spacing between two adjacent graduation lines 14, yet more narrowly every 1/6 of the spacing between two adjacent graduation lines 14, yet more narrowly every 1/5 of the spacing between two adjacent graduation lines 14, yet more narrowly every 1/4 of the spacing between two adjacent graduation lines 14, yet more narrowly every 1/2 of the spacing between two adjacent graduation lines 14, yet more narrowly every one of the graduation line 14, yet more narrowly every 2 of the graduation lines 14, yet more narrowly every 4 of the graduation lines 14, yet more narrowly every 5 of the graduation lines 14, yet more narrowly every 10 of the graduation lines 14. The syringe 1 may only be in the engaged configuration at certain volumes of the syringe 1. For example, the syringe 1 may only be in the engaged configuration at volumes ranging from approximately half of the capacity of the syringe 1 to the full capacity of the syringe 1. The syringe 1 may typically be filled to at least half of the capacity of the syringe 1, so it may not be necessary or desired to enable the engaged configuration at volumes less than half the capacity of the syringe 1. The plunger thread face 20 may only be present for portions of the plunger 8 to control at what points the syringe 1 can enter the engaged configuration. The plunger thread face 20 may be continuous and/or discontinuous.

The plunger thread pitch 26 and/or the barrel thread pitch 38 may be greater than approximately 1/10 of the spacing between adjacent graduation lines 14, yet more narrowly larger than approximately 1/8 of the spacing between adjacent graduation lines 14, yet more narrowly larger than approximately 1/5 of the spacing between adjacent graduation lines 14, yet more narrowly larger than approximately 1/4 of the spacing between adjacent graduation lines 14, yet more narrowly larger than approximately 1/2 of the spacing between adjacent graduation lines 14, yet more narrowly larger than approximately the spacing between adjacent graduation lines 14, yet more narrowly larger than approximately twice the spacing between adjacent graduation lines 14, yet more narrowly larger than approximately three times the spacing between adjacent graduation lines 14, yet more narrowly larger than approximately four times the spacing between adjacent graduation lines 14, yet more narrowly larger than approximately five times the spacing between adjacent graduation lines 14 and/or yet more narrowly larger than approximately ten times the spacing between adjacent graduation lines 14. The plunger thread pitch 26 and/or the barrel thread pitch 38 may be less than approximately ten times the spacing between adjacent graduation lines 14, yet more narrowly less than approximately eight times the spacing between adjacent graduation lines 14, yet more narrowly less than approximately six times the spacing between adjacent graduation lines 14, yet more narrowly less than approximately five times the spacing between adjacent graduation lines 14, yet more narrowly less than approximately four times the spacing between adjacent graduation lines 14, yet more narrowly less than approximately two times the spacing between adjacent graduation lines 14, yet more narrowly less than approximately the spacing between adjacent graduation lines 14, yet more narrowly less than approximately 1/2 the spacing between adjacent graduation lines 14, yet more narrowly less than approximately 1/3 the spacing between adjacent graduation lines 14, yet more narrowly less than approximately 1/4 the spacing between adjacent graduation lines 14, yet more narrowly less than approximately 1/5 the spacing between adjacent graduation lines 14 and/or yet more narrowly less than approximately 1/10 the spacing between adjacent graduation lines 14. When the syringe 1 transitions between the disengaged configuration and/or the engaged configuration, the plunger 8 may advance and/or retract at most approximately half of plunger thread pitch 26 and/or the barrel thread pitch 38. The plunger 8 may advance and/or retract when the barrel thread 65 is engaging with the plunger thread 66. When the plunger thread 66 engages with the barrel thread 65, it may be desired that the plunger 8 is biased toward advancing distally instead of proximally. When the plunger thread 66 engages with the barrel thread 65, it may be desired that the plunger 8 translates less than the spacing between two adjacent graduation lines 14.

The minimum axially oriented distance from the barrel engagement region 50 to the barrel proximal end 98 may be a barrel proximal to engagement distance 97. The minimum axially oriented distance from the barrel engagement region 50 to the barrel flange 11 may be a barrel flange to engagement distance 99. The barrel proximal to engagement distance 97, the radius of the barrel engagement transition region 85, the barrel flange to engagement distance 99, the plunger thread radial distance 75, the plunger flat width 28, the plunger thread arc length 35, the barrel nut height 25, the barrel nut width 24, the barrel thread radial distance 76, the barrel thread arc length 69, the plunger thread face arc length 77 and/or the barrel thread face arc length 78 can be larger than 0.05 in (1.27 mm), yet more narrowly larger than about 0.10 in (2.54 mm), yet more narrowly larger than about 0.15 in (3.81 mm), yet more narrowly larger than about 0.20 in (5.08 mm), yet more narrowly larger than about 0.25 in (6.35 mm), yet more narrowly larger than about 0.30 in (7.62 mm), yet more narrowly larger than about 035 in (8.89 mm), yet more narrowly larger than about 0.4 in (10.16 mm), yet more narrowly larger than about 0.45 in (11.43 mm), yet more narrowly larger than about 0.5 in (12.7 mm), yet more narrowly larger than about 0.55 in (13.97 mm), yet more narrowly larger than about 0.6 in (15.24 mm), yet more narrowly larger than about 0.65 in (16.51 mm), yet more narrowly larger than about 0.7 in (17.78 mm), yet more narrowly larger than about 0.75 in (19.05 mm), yet more narrowly larger than about 0.8 in (20.32 mm), yet more narrowly larger than about 0.9 in (22.86 mm), yet more narrowly larger than about 1.0 in (25.4 mm), yet more narrowly larger than about 1.1 in (27.94 mm) or yet more narrowly larger than about 1.2 in (30.48 mm). The barrel proximal to engagement distance 97, the barrel flange to engagement distance 99, the plunger thread radial distance 75, the plunger flat width 28, the plunger thread arc length 35, the radius of the barrel engagement transition region 85, the barrel nut height 25, the barrel nut width 24, the barrel thread radial distance 76, the barrel thread arc length 69, the plunger thread face arc length 77 and/or the barrel thread face arc length 78 can be smaller than 1.2 in (30.48 mm), yet more narrowly smaller than about 1.1 in (27.94 mm), yet more narrowly smaller than about 1.0 in (25.4 mm), yet more narrowly smaller than about 0.9 in (22.86 mm), yet more narrowly smaller than about 0.8 in (20.32 mm), yet more narrowly smaller than about 0.75 in (19.05 mm), yet more narrowly smaller than about 0.7 in (17.78 mm), yet more narrowly smaller than about 0.65 in (16.51 mm), yet more narrowly smaller than about 0.6 in (15.24 mm), yet more narrowly smaller than about 0.55 in (13.97 mm), yet more narrowly smaller than about 0.5 in (12.7 mm), yet more narrowly smaller than about 0.45 in (11.43 mm), yet more narrowly smaller than about 0.4 in (10.16 mm), yet more narrowly smaller than about 0.35 in (8.89 mm), yet more narrowly smaller than about 0.3 in (7.62 mm), yet more narrowly smaller than about 0.25 in (6.35 mm), yet more narrowly smaller than about 0.2 in (5.08 mm), yet more narrowly smaller than about 0.15 in (3.81 mm), yet more narrowly smaller than about Olin (2.54 mm) or yet more narrowly smaller than about 0.05 in (1.27 mm). The inside and/or outside diameter of the barrel 5 can vary in different locations.

The syringe 1 or any or all elements of the tool and/or other tools or apparatuses described herein can be made from or coated with, for example, rubber, thermoplastic elastomer (TPE), polyisoprene rubber, latex-free elastomer, silicone, liquid silicone rubber (LSR), polypropylene, LDPE, HDPE, single or multiple stainless steel alloys, steel, spring steel, nickel titanium alloys (e.g., Nitinol), cobalt-chrome alloys (e.g., ELGILOY® from Elgin Specialty Metals, Elgin, IL; CONICHROME® from Carpenter Metals Corp., Wyomissing, PA), nickel-cobalt alloys (e.g., MP35N® from Magellan Industrial Trading Company, Inc., Westport, CT), molybdenum alloys (e.g., molybdenum TZM alloy), tungsten-rhenium alloys, polymers such as polyethylene teraphathalate (PET), polyester (e.g., DACRON® from E. I. Du Pont de Nemours and Company, Wilmington, Del.), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, NJ, or DYNEEMA® from Royal DSM N.V, Heerlen, the Netherlands), polytetrafluoroethylene (PTFE), Parylene poly(p-xylylene) polymers, Parylene N, Parylene C, Parylene D, expanded PTFE (ePTFE), polyether ketone (PEK), polyether ether ketone (PEEK), polycarbonate (PC), Acrylonitrile Butadiene Styrene (ABS), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, MA), polyvinyl chloride (PVC), Nylon, Vinyl, polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone), a material with high strength (60 ksi) and biocompatibility, any of the other materials listed herein or combinations thereof. Examples of radiopaque materials are barium sulfate, zinc oxide, titanium, stainless steel, nickel-titanium alloys, tantalum and gold. The device can be made from substantially 100% PEEK, substantially 100% titanium or titanium alloy, or combinations thereof.

U.S. Pat. No. 9,561,327 issued on Feb. 7, 2017 is incorporated by reference herein in its entirety.

It is apparent to one skilled in the art that various changes and modifications can be made to this disclosure, and equivalents employed, or combinations of any of the disclosed elements, characteristics, features, devices, tools, steps, or methods without departing from the spirit and scope of the disclosure. Any of the disclosed elements, characteristics, features, devices, tools, steps, or methods can be present as a singular or as a plurality regardless of whether the elements, characteristics, features, devices, steps, or methods are explicitly disclosed herein as being singular or as a plurality. Elements shown with any variation are exemplary for the specific variation and can be used on other variations within this disclosure.

I claim:

1. A syringe for dispensing a fluid comprising:

a barrel having a barrel body having a barrel thread face across a barrel thread face arc angle at a first cross-section, wherein the barrel thread face has an internal barrel thread integral with the barrel body, and wherein an inner cross-section of the barrel at the first cross-section has a first minimum inner diameter and a first maximum inner diameter, and wherein the inner cross-section of the barrel at a second cross-section has a second minimum inner diameter and a second maximum inner diameter, and wherein the first minimum inner diameter is smaller than the second minimum inner diameter, and wherein the first maximum inner diameter is larger than the second maximum inner diameter, wherein the inner cross-section of the barrel at a third cross-section has a third minimum inner diameter and a third maximum inner diameter, and wherein a longitudinal position of the third cross-section is on an opposite side of a longitudinal position of the first cross-section from a longitudinal position of the second cross-section, and wherein the first minimum inner diameter is smaller than the third minimum inner diameter; and wherein the second minimum inner diameter is equal to the third minimum inner diameter; and wherein the second maximum inner diameter is equal to the third maximum inner diameter, and a plunger having a plunger body, wherein at least a length of the plunger body is in the barrel, wherein the plunger has a plunger thread face across a plunger thread face arc angle at the first cross-section, wherein the plunger thread face has first and second external plunger threads integral with the plunger body; and wherein the barrel threads are perpendicular with a longitudinal axis of the syringe.

2. The syringe of claim 1, wherein in a first configuration the plunger is rotated 0 degrees with respect to the barrel and the barrel is at a first longitudinal position with respect to the plunger, wherein in a second configuration the plunger is rotated 360 degrees with respect to the barrel and the barrel is at the first longitudinal position with respect to the plunger, and wherein in the first configuration the internal barrel thread is engaged with the first and second external plunger threads, and wherein in the second configuration the internal barrel thread is engaged with first and second external plunger threads.

3. The syringe of claim 1, further comprising a detent extending from the barrel body at the first minimum inner diameter.

4. The syringe of claim 1, wherein an inner surface of the barrel has a lofted transition from the third cross-section to the first cross-section and has a lofted transition from the first cross-section to the second cross-section.

5. A method for dispensing a fluid using a syringe comprising a plunger having a plunger body having a plunger thread integral with the plunger body and a barrel having a barrel body having a barrel thread integral with the barrel body at a first cross-section, wherein the method comprises:

longitudinally depressing the plunger with respect to the barrel when the plunger starts at a first angular position, and wherein the depressing results in longitudinal translation of the plunger with respect to the barrel, and wherein the depressing comprises contacting the barrel thread with the plunger;

rotating the plunger with respect to the barrel when the plunger starts at the first angular position with respect to the barrel, wherein the rotating comprises engaging the plunger thread with the barrel thread; and then pressing the plunger with respect to the barrel when the plunger starts at a second angular position with respect to the barrel, wherein the pressing of the plunger comprises no longitudinal translation of the plunger with respect to the barrel; and wherein an inner cross-section of the barrel at the first cross-section has a first minimum inner diameter, and wherein the inner cross-section of the barrel at a second cross-section has a second minimum inner diameter, and wherein the first minimum inner diameter is smaller than the second minimum inner diameter, wherein the inner cross-section of the barrel at a third cross-section has a third minimum inner diameter, and wherein a longitudinal position of the third cross-section is on an opposite side of a longitudinal position of the first cross-section from a longitudinal position of the second cross-section, and wherein the first minimum inner diameter is smaller than the third minimum inner diameter.

6. The method of claim 5, wherein the rotating does not longitudinally move the plunger with respect to the barrel.

7. The method of claim 5, wherein the pressing and the rotating comprise the plunger being threadably engaged with the barrel, and wherein the depressing comprises the plunger being threadably disengaged from the barrel.

8. The method of claim 5, wherein the rotating comprises rotating more than 360 degrees.

9. The method of claim 5, wherein a first radial distance from the plunger thread to a longitudinal axis of the plunger when rotating the plunger is equal to a second radial distance from the plunger thread to the longitudinal axis of the plunger when depressing the plunger; wherein a third radial distance from the barrel thread to the longitudinal axis of the plunger when rotating the plunger is equal to a fourth radial distance from the barrel thread to the longitudinal axis of the plunger when depressing the plunger.

10. The method of claim 5, wherein the pressing, rotating and depressing start with the plunger at a first longitudinal position with respect to the barrel.

11. The method of claim 5, wherein the barrel has a first outer radius, and wherein the rotating comprises deforming the barrel, and wherein the deforming the barrel comprises increasing the first outer radius.

* * * * *